(12) United States Patent
Abunassar et al.

(10) Patent No.: US 12,109,115 B2
(45) Date of Patent: Oct. 8, 2024

(54) WIDE CLIP WITH DEFORMABLE WIDTH

(71) Applicant: EVALVE, INC., Santa Clara, CA (US)

(72) Inventors: Chad Abunassar, San Francisco, CA (US); Santosh Prabhu, Sunnyvale, CA (US); Casey Barbarino, San Francisco, CA (US); Jessie Garcia, Newark, CA (US); Gabriel Gonzales, Milpitas, CA (US); Brandon Chu, San Francisco, CA (US); Tamer M. Mahmoud, Sunnyvale, CA (US); Michael Wei, Redwood City, CA (US)

(73) Assignee: EVALVE, INC., Santa Clara, CA (US)

( * ) Notice: Subject to any disclaimer, the term of this patent is extended or adjusted under 35 U.S.C. 154(b) by 884 days.

(21) Appl. No.: 17/124,259

(22) Filed: Dec. 16, 2020

(65) Prior Publication Data

US 2021/0186698 A1 Jun. 24, 2021

Related U.S. Application Data

(60) Provisional application No. 62/949,563, filed on Dec. 18, 2019.

(51) Int. Cl.
*A61F 2/24* (2006.01)
*A61B 17/122* (2006.01)

(52) U.S. Cl.
CPC ............ *A61F 2/246* (2013.01); *A61B 17/122* (2013.01); *A61F 2/2454* (2013.01); *A61F 2/2463* (2013.01); *A61F 2/2466* (2013.01); *A61F 2/2445* (2013.01); *A61F 2210/0014* (2013.01); *A61F 2220/0091* (2013.01)

(58) Field of Classification Search
CPC ...... A61F 2/2454; A61F 2/246; A61F 2/2463; A61F 2/2466; A61B 17/122
See application file for complete search history.

(56) References Cited

U.S. PATENT DOCUMENTS

| | | |
|---|---|---|
| 3,378,010 A | 4/1968 | Codling et al. |
| 3,874,388 A | 4/1975 | King et al. |
| 4,007,743 A | 2/1977 | Blake |

(Continued)

FOREIGN PATENT DOCUMENTS

| | | |
|---|---|---|
| CA | 2 296 317 C | 1/2009 |
| CN | 106102599 | 11/2016 |

(Continued)

OTHER PUBLICATIONS

International Search Report and Written Opinion mailed Mar. 22, 2021 in International Application No. PCT/US2020/065422.

*Primary Examiner* — William H Matthews
(74) *Attorney, Agent, or Firm* — SLEMAN & LUND LLP

(57) ABSTRACT

Fixation device for fixation of leaflets of a heart valve includes a central assembly and at least one arm moveably coupled relative to the central assembly. The at least one arm includes a deformable frame having a first end and a second end and a longitudinal axis defined therebetween, the second end being moveable between a closed position and an open position. The deformable frame further includes first and second deformable flex portions, each flex portion extending along a respective lateral side of the deformable frame and having a deformed condition and an undeformed condition, and each flex portion having an outer lateral edge. The at least one arm has a maximum deformed arm lateral cross-dimension with the flex portions in the deformed condition.

21 Claims, 19 Drawing Sheets

(56) References Cited

U.S. PATENT DOCUMENTS

| | | |
|---|---|---|
| 4,055,861 A | 11/1977 | Carpentier et al. |
| 4,327,736 A | 5/1982 | Inoue |
| 4,340,091 A | 7/1982 | Skelton et al. |
| 4,657,024 A | 4/1987 | Coneys |
| 4,693,248 A | 9/1987 | Failla |
| 4,716,886 A | 1/1988 | Schulman et al. |
| 4,795,458 A | 1/1989 | Regan |
| 4,809,695 A | 3/1989 | Gwathmey et al. |
| 4,930,674 A | 6/1990 | Barak |
| 5,002,562 A | 3/1991 | Oberlander |
| 5,069,679 A | 12/1991 | Taheri |
| 5,098,440 A | 3/1992 | Hillstead |
| 5,125,895 A | 6/1992 | Buchbinder et al. |
| 5,147,370 A | 9/1992 | McNamara et al. |
| 5,171,259 A | 12/1992 | Inoue |
| 5,222,963 A | 6/1993 | Brinkerhoff et al. |
| 5,271,544 A | 12/1993 | Fox et al. |
| 5,327,905 A | 7/1994 | Avitall |
| 5,330,501 A | 7/1994 | Tovey et al. |
| 5,334,217 A | 8/1994 | Das |
| 5,363,861 A | 11/1994 | Edwards et al. |
| 5,389,077 A | 2/1995 | Melinyshyn et al. |
| 5,403,326 A | 4/1995 | Harrison et al. |
| 5,425,744 A | 6/1995 | Fagan et al. |
| 5,450,860 A | 9/1995 | O'Connor |
| 5,452,837 A | 9/1995 | Williamson, IV et al. |
| 5,456,400 A | 10/1995 | Shichman et al. |
| 5,456,674 A | 10/1995 | Bos et al. |
| 5,478,353 A | 12/1995 | Yoon |
| 5,542,949 A | 8/1996 | Yoon |
| 5,562,678 A | 10/1996 | Booker |
| 5,601,224 A | 2/1997 | Bishop et al. |
| 5,601,574 A | 2/1997 | Stefanchik et al. |
| 5,607,462 A | 3/1997 | Imran |
| 5,607,471 A | 3/1997 | Seguin et al. |
| 5,609,598 A | 3/1997 | Laufer et al. |
| 5,611,794 A | 3/1997 | Sauer et al. |
| 5,636,634 A | 6/1997 | Kordis et al. |
| 5,695,504 A | 12/1997 | Gifford, III et al. |
| 5,713,911 A | 2/1998 | Racenet et al. |
| 5,716,417 A | 2/1998 | Girard et al. |
| 5,741,297 A | 4/1998 | Simon |
| 5,755,778 A | 5/1998 | Kleshinski |
| 5,782,239 A | 7/1998 | Webster, Jr. |
| 5,797,960 A | 8/1998 | Stevens et al. |
| 5,810,847 A | 9/1998 | Laufer et al. |
| 5,814,097 A | 9/1998 | Sterman et al. |
| 5,843,178 A | 12/1998 | Vanney et al. |
| 5,849,019 A | 12/1998 | Yoon |
| 5,855,601 A | 1/1999 | Bessler et al. |
| 5,976,159 A | 11/1999 | Bolduc et al. |
| 6,015,417 A | 1/2000 | Reynolds, Jr. |
| 6,048,351 A | 4/2000 | Gordon et al. |
| 6,079,414 A | 6/2000 | Roth |
| 6,117,144 A | 9/2000 | Nobles et al. |
| 6,120,496 A | 9/2000 | Whayne et al. |
| 6,149,658 A | 11/2000 | Gardiner et al. |
| 6,165,183 A | 12/2000 | Kuehn et al. |
| 6,182,664 B1 | 2/2001 | Cosgrove |
| 6,193,734 B1 | 2/2001 | Bolduc et al. |
| 6,200,315 B1 | 3/2001 | Gaiser et al. |
| 6,217,528 B1 | 4/2001 | Koblish et al. |
| 6,269,819 B1 | 8/2001 | Oz et al. |
| 6,290,674 B1 | 9/2001 | Roue et al. |
| 6,312,447 B1 | 11/2001 | Grimes |
| 6,332,880 B1 | 12/2001 | Yang et al. |
| 6,346,074 B1 | 2/2002 | Roth |
| 6,419,696 B1 | 7/2002 | Ortiz et al. |
| 6,461,366 B1 | 10/2002 | Seguin |
| 6,482,224 B1 | 11/2002 | Michler et al. |
| 6,496,420 B2 | 12/2002 | Manning |
| 6,544,215 B1 | 4/2003 | Bencini et al. |
| 6,551,303 B1 | 4/2003 | Van Tassel et al. |
| 6,575,971 B2 | 6/2003 | Hauck et al. |
| 6,599,311 B1 | 7/2003 | Biggs et al. |
| 6,626,930 B1 | 9/2003 | Allen et al. |
| 6,629,534 B1 | 10/2003 | St. Goar et al. |
| 6,669,687 B1 | 12/2003 | Saadat |
| 6,695,866 B1 | 2/2004 | Kuehn et al. |
| 6,719,767 B1 | 4/2004 | Kimblad |
| 6,752,813 B2 | 6/2004 | Goldfarb et al. |
| 6,770,083 B2 | 8/2004 | Seguin |
| 6,797,002 B2 | 9/2004 | Spence et al. |
| 6,837,867 B2 | 1/2005 | Kortelling |
| 6,855,137 B2 | 2/2005 | Bon |
| 6,875,224 B2 | 4/2005 | Grimes |
| 6,908,481 B2 | 6/2005 | Cribier |
| 6,926,730 B1 | 8/2005 | Nguyen et al. |
| 7,011,669 B2 | 3/2006 | Kimblad |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,226,467 B2 | 6/2007 | Lucatero et al. |
| 7,556,632 B2 | 7/2009 | Zadno |
| 7,563,267 B2 | 7/2009 | Goldfarb et al. |
| 7,569,062 B2 | 8/2009 | Kuehn et al. |
| 7,604,646 B2 | 10/2009 | Goldfarb et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,736,388 B2 | 6/2010 | Goldfarb et al. |
| 7,811,296 B2 | 10/2010 | Goldfarb et al. |
| 7,972,323 B1 | 7/2011 | Bencini et al. |
| 7,981,139 B2 | 7/2011 | Martin et al. |
| 8,057,493 B2 | 11/2011 | Goldfarb et al. |
| 8,062,313 B2 | 11/2011 | Kimblad |
| 8,118,822 B2 | 2/2012 | Schaller et al. |
| 8,216,230 B2 | 7/2012 | Hauck et al. |
| 8,216,256 B2 | 7/2012 | Raschdorf, Jr. et al. |
| 8,303,608 B2 | 11/2012 | Goldfarb et al. |
| 8,500,761 B2 | 8/2013 | Goldfarb et al. |
| 8,734,505 B2 | 5/2014 | Goldfarb et al. |
| 8,740,920 B2 | 6/2014 | Goldfarb et al. |
| 9,510,829 B2 | 12/2016 | Goldfarb et al. |
| 10,076,415 B1 | 9/2018 | Metchik et al. |
| 10,105,222 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,231,837 B1 | 3/2019 | Metchik et al. |
| 10,238,493 B1 | 3/2019 | Metchik et al. |
| 10,245,144 B1 | 4/2019 | Metchik et al. |
| D847,983 S | 5/2019 | Ho et al. |
| 10,314,586 B2 | 6/2019 | Greenberg et al. |
| 10,413,408 B2 | 9/2019 | Krone et al. |
| 10,507,109 B2 | 12/2019 | Metchik et al. |
| 10,517,726 B2 | 12/2019 | Chau et al. |
| 10,524,792 B2 | 1/2020 | Hernandez et al. |
| 10,595,997 B2 | 3/2020 | Metchik et al. |
| 10,646,342 B1 | 5/2020 | Marr et al. |
| 10,779,837 B2 | 9/2020 | Lee et al. |
| D902,403 S | 11/2020 | Marsot et al. |
| 10,856,988 B2 | 12/2020 | McNiven et al. |
| 11,464,636 B2 | 10/2022 | Abunassar |
| 11,660,189 B2 | 5/2023 | Abunassar |
| 2002/0013571 A1 | 1/2002 | Goldfarb et al. |
| 2002/0183787 A1 | 12/2002 | Wahr et al. |
| 2003/0069593 A1 | 4/2003 | Tremulis et al. |
| 2003/0167071 A1 | 9/2003 | Martin et al. |
| 2004/0034365 A1 | 2/2004 | Lentz et al. |
| 2004/0044350 A1 | 3/2004 | Martin et al. |
| 2005/0267493 A1 | 12/2005 | Schreck et al. |
| 2006/0020275 A1 | 1/2006 | Goldfarb |
| 2006/0089671 A1 | 4/2006 | Goldfarb |
| 2007/0038293 A1 | 2/2007 | St. Goar et al. |
| 2011/0004227 A1 | 1/2011 | Goldfarb et al. |
| 2017/0042546 A1 | 2/2017 | Goldfarb et al. |
| 2017/0049455 A1 | 2/2017 | Seguin |
| 2017/0239048 A1 | 8/2017 | Goldfarb et al. |
| 2017/0265994 A1 | 9/2017 | Krone |
| 2018/0021133 A1 | 1/2018 | Barbarino |
| 2018/0036119 A1 | 2/2018 | Wei et al. |
| 2018/0092661 A1 | 4/2018 | Prabhu |

(56) References Cited

U.S. PATENT DOCUMENTS

| | | |
|---|---|---|
| 2018/0146964 A1 | 5/2018 | Garcia et al. |
| 2018/0235657 A1 | 8/2018 | Abunassar |
| 2018/0242976 A1 | 8/2018 | Kizuka |
| 2018/0243086 A1 | 8/2018 | Barbarino et al. |
| 2018/0296329 A1 | 10/2018 | Dixon |
| 2018/0325671 A1 | 11/2018 | Abunassar et al. |
| 2018/0344460 A1 | 12/2018 | Wei |
| 2018/0353181 A1 | 12/2018 | Wei |
| 2018/0360457 A1 | 12/2018 | Ellis et al. |
| 2019/0053803 A1 | 2/2019 | Ketai et al. |
| 2019/0083251 A1 | 3/2019 | Hariton |
| 2019/0125536 A1 | 5/2019 | Prabhu et al. |
| 2019/0151041 A1 | 5/2019 | Ho et al. |
| 2019/0151089 A1 | 5/2019 | Wei |
| 2019/0159899 A1 | 5/2019 | Marsot et al. |
| 2019/0167197 A1 | 6/2019 | Abunassar et al. |
| 2019/0175182 A1 | 6/2019 | Goldfarb |
| 2019/0183571 A1 | 6/2019 | De Marchena |
| 2019/0209293 A1 | 7/2019 | Metchik et al. |
| 2019/0209297 A1 | 7/2019 | Metchik et al. |
| 2019/0247187 A1 | 8/2019 | Kizuka |
| 2019/0274831 A1 | 9/2019 | Prabhu |
| 2019/0321597 A1 | 10/2019 | Van Hoven et al. |
| 2019/0343630 A1 | 11/2019 | Kizuka |
| 2019/0350702 A1 | 11/2019 | Hernandez |
| 2019/0350710 A1 | 11/2019 | Ketai et al. |
| 2019/0365536 A1 | 12/2019 | Prabhu |
| 2020/0000473 A1 | 1/2020 | Dell et al. |
| 2020/0060687 A1 | 2/2020 | Hernández et al. |
| 2020/0078173 A1 | 3/2020 | McNiven et al. |
| 2020/0113678 A1 | 4/2020 | McCann et al. |
| 2020/0121460 A1 | 4/2020 | Dale et al. |
| 2020/0121894 A1 | 4/2020 | Prabhu et al. |
| 2020/0187942 A1 | 6/2020 | Wei |
| 2020/0205829 A1 | 7/2020 | Wei |
| 2020/0245998 A1 | 8/2020 | Basude et al. |
| 2020/0261107 A1 | 8/2020 | Cohen |
| 2020/0281591 A1 | 9/2020 | Krone et al. |
| 2020/0323528 A1 | 10/2020 | Khairkhahan |
| 2020/0323549 A1 | 10/2020 | Goldfarb et al. |
| 2020/0323634 A1 | 10/2020 | Von Oepen et al. |
| 2020/0360018 A1 | 11/2020 | Dell et al. |
| 2020/0367871 A1 | 11/2020 | Van Hoven et al. |
| 2021/0015614 A1 | 1/2021 | Kizuka |
| 2021/0106419 A1 | 4/2021 | Abunassar |
| 2021/0145574 A1 | 5/2021 | Childs |
| 2021/0186698 A1 | 6/2021 | Abunassar |

FOREIGN PATENT DOCUMENTS

| | | |
|---|---|---|
| CN | 207368927 | 5/2018 |
| CN | 114176837 A | 3/2022 |
| CN | 216221859 U | 4/2022 |
| CN | 115300181 A | 11/2022 |
| EP | 0 558 031 B1 | 9/1993 |
| EP | 1 383 448 B1 | 6/2008 |
| FR | 2 768 324 A1 | 3/1999 |
| FR | 2 768 325 B1 | 11/1999 |
| JP | 2008517732 A | 5/2008 |
| JP | 6732663 B2 | 7/2020 |
| WO | WO 91/01689 A1 | 2/1991 |
| WO | WO 92/12690 A1 | 8/1992 |
| WO | WO 94/018893 A1 | 9/1994 |
| WO | WO 96/32882 A1 | 10/1996 |
| WO | WO 97/27807 A1 | 8/1997 |
| WO | WO 98/07375 A1 | 2/1998 |
| WO | WO 99/07354 A2 | 2/1999 |
| WO | WO 99/13777 A1 | 3/1999 |
| WO | WO 99/15223 A1 | 4/1999 |
| WO | WO 00/03759 A2 | 1/2000 |
| WO | WO 00/60995 A2 | 10/2000 |
| WO | WO 01/28432 A1 | 4/2001 |
| WO | WO 03/020179 A1 | 3/2003 |
| WO | WO 03/049619 A2 | 6/2003 |
| WO | WO 2015/057289 A1 | 4/2015 |
| WO | 2016099650 A1 | 6/2016 |
| WO | WO 2016/178722 A1 | 11/2016 |
| WO | WO 2018/093663 A1 | 5/2018 |
| WO | 2019129024 | 7/2019 |
| WO | 2021011531 A1 | 1/2021 |
| WO | 2021027588 A1 | 2/2021 |

WIDE CLIP WITH DEFORMABLE WIDTH

FIELD OF DISCLOSED SUBJECT MATTER

The disclosed subject matter is directed to medical devices for the endovascular, percutaneous or minimally invasive surgical treatment of bodily tissues, such as tissue approximation or valve repair. More particularly, the present disclosure relates to repair of valves of the heart and venous valves.

Surgical repair of bodily tissues can involve tissue approximation and fastening of such tissues in the approximated arrangement. When repairing valves, tissue approximation includes coapting the leaflets of the valves in a therapeutic arrangement which can then be maintained by fastening or fixing the leaflets. Such coaptation can be used to treat regurgitation, which commonly occurs in the mitral valve and in the tricuspid valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the mitral valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles or the left ventricular wall can be damaged or otherwise dysfunctional. Commonly, the valve annulus can be damaged, dilated, or weakened limiting the ability of the mitral valve to close adequately against the high pressures of the left ventricle.

DESCRIPTION OF RELATED ART

Treatments for mitral valve regurgitation rely on valve replacement or repair including leaflet and annulus remodeling, the latter generally referred to as valve annuloplasty. Another technique for mitral valve repair, which relies on suturing adjacent segments of the opposed valve leaflets together is referred to as the "bow-tie" or "edge-to-edge" technique. Preferably, the use of devices and systems should not require open chest access and, rather, be capable of being performed either endovascularly, i.e., using devices, such as a catheter, which are advanced to the heart from a point in the patient's vasculature remote from the heart. Furthermore, such devices and systems should allow for repositioning and optional removal of a fixation device (i.e., valve repair clip) prior to fixation to ensure optimal placement. Such devices and systems likewise can be useful for repair of tissues in the body other than heart valves.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to a fixation device for treating a patient.

In accordance with the disclosed subject matter, a fixation device for fixation of leaflets of a heart valve includes a central assembly and at least one arm moveably coupled relative to the central assembly. The at least one arm includes a deformable frame having a first end and a second end and a longitudinal axis defined therebetween, the second end being moveable between a closed position and an open position. The deformable frame further includes first and second deformable flex portions, each flex portion extending along a respective lateral side of the deformable frame and having a deformed condition and an undeformed condition, and each flex portion having an outer lateral edge. The at least one arm has a maximum deformed arm lateral cross-dimension with the flex portions in the deformed condition and a maximum undeformed arm width defined between the outer lateral edge of the first flex portion and the outer lateral edge of the second flex portion in the undeformed condition. The ratio of the maximum deformed arm lateral cross-dimension to the maximum undeformed arm width is at least 1:1.3. The fixation device further includes at least one gripping element moveable relative to the at least one arm to capture a native leaflet therebetween.

In accordance with the disclosed subject matter, the deformable frame can further include a trough defined along the longitudinal axis, and further the first flex portion can include a deformable first wing extension extending laterally from a first lateral side of the trough and the second flex portion includes a deformable second wing extension extending laterally from a second lateral side of the trough. The first and second wing extensions each can have a second end edge extending laterally from the second end of the deformable frame at a second end angle defined between the second end edge and the longitudinal axis, wherein the second end angle is between 15 and 45 degrees. The deformable frame, including the trough and the first and second wing extensions, can be a single piece construction. Additionally, the first and second wing extensions can each include at least one notch defined along a respective lateral edge thereof. Additionally or alternatively, the first and second wing extensions can each comprise an open wing extension frame defining a wing opening therethrough in plan view. The maximum undeformed arm width can be proximate the second end of the deformable frame.

Furthermore, with the trough defined along the longitudinal axis, the trough can have a greater width between opposing lateral sides of the trough along a length of the arm proximate the maximum undeformed arm width. In this manner, at least one gripping element can have a first end coupled to a portion of the fixation device and a second end moveable relative to the at least one arm, wherein the gripping element can have a greater width proximate the second end of the gripping element. The first and second wing extensions can be made of shape memory material.

In accordance with another aspect of the disclosed subject matter, the first flex portion can comprise a deformable first flank member extending longitudinally along a first lateral side of the deformable frame and the second flex portion can comprise a deformable second flank member extending longitudinally along a second lateral side of the deformable frame, the first and second flank members in the deformed condition being aligned generally parallel with longitudinal axis. The first and second flank members in the undeformed condition can each have at least a length thereof extending outwardly away from the longitudinal axis.

The deformable frame can further include a first strut extending laterally from the first flank member to the second flank member, wherein the first strut comprises a hinge portion having a compressed configuration with the deformable frame in the deformed condition and an extended configuration with the deformable frame in the undeformed condition. The hinge portion can be biased toward the extended condition. The deformable frame can further comprise an end strut extending laterally from the first flank member to the second flank member at the second end of the deformable frame. The end strut can include a hinge portion having a compressed configuration with the deformable frame in the deformed condition and an extended configuration with the deformable frame in the undeformed condition, the first strut can be spaced longitudinally from the end strut.

Alternatively, the deformable frame can include a first strut extending laterally from the first flank member toward the second flank member and a second strut extending laterally from the second flank member toward the first strut member. The deformable frame can further comprise an end strut extending laterally from the first flank member to the second flank member at the second end of the deformable frame. The end strut can comprise a hinge portion having a compressed configuration with the deformable frame in the deformed condition and an extended configuration with the deformable frame in the undeformed condition. The first and second struts can be in overlapping sliding arrangement for movement relative each other between the deformed condition and the undeformed condition. Alternatively, the first and second struts can be laterally spaced from each other with the deformable frame in the undeformed condition. The fixation device can further include a middle support member extending parallel with the longitudinal axis between the first and second flank members.

As also embodied herein, the deformable frame can include a plurality of first struts extending laterally from the first flank member toward the second flank member and a plurality of second struts extending laterally from the second flank member toward the first strut member. The plurality of first struts and the plurality of second struts can be configured to interlock with each other in the deformed condition and release from each other in the undeformed condition. The first and second flank members can each have a tapered portion proximate the second end of the deformable frame. Additionally or alternatively, the at least one arm can comprise an expandable mesh portion extending between the first and second flank members. The first and second flank members can comprise shape memory material.

In accordance with another aspect of the disclosed subject matter, a system for fixation of leaflets of a heart valve includes a guide catheter having an inner diameter, and a fixation device for fixation of leaflets of a heart valve. The device including a central assembly and at least one arm moveably coupled relative to the central assembly. The at least one arm includes a deformable frame having a first end and a second end and a longitudinal axis defined therebetween. The second end is moveable between a closed position and an open position. The deformable frame further includes first and second deformable flex portions. Each flex portion extends along a respective lateral side of the deformable frame and has a deformed condition and an undeformed condition. Each flex portion has a lateral outer edge. The at least one arm has a maximum deformed arm lateral cross-dimension with the flex portions in the deformed condition and a maximum undeformed arm width defined between the outer lateral edge of the first flex portion and the outer lateral edge of the second flex portion in the undeformed condition. The ratio of the maximum deformed arm lateral cross-dimension to the maximum undeformed arm width is at least 1:1.3. The fixation device further includes at least one gripping element moveable relative to the at least one arm to capture a native leaflet therebetween.

The maximum deformed arm lateral cross-dimension can be less than the inner diameter of the guide catheter, and the maximum undeformed arm width can be greater than the inner diameter of the guide catheter.

DETAILED DESCRIPTION

Figure 1:
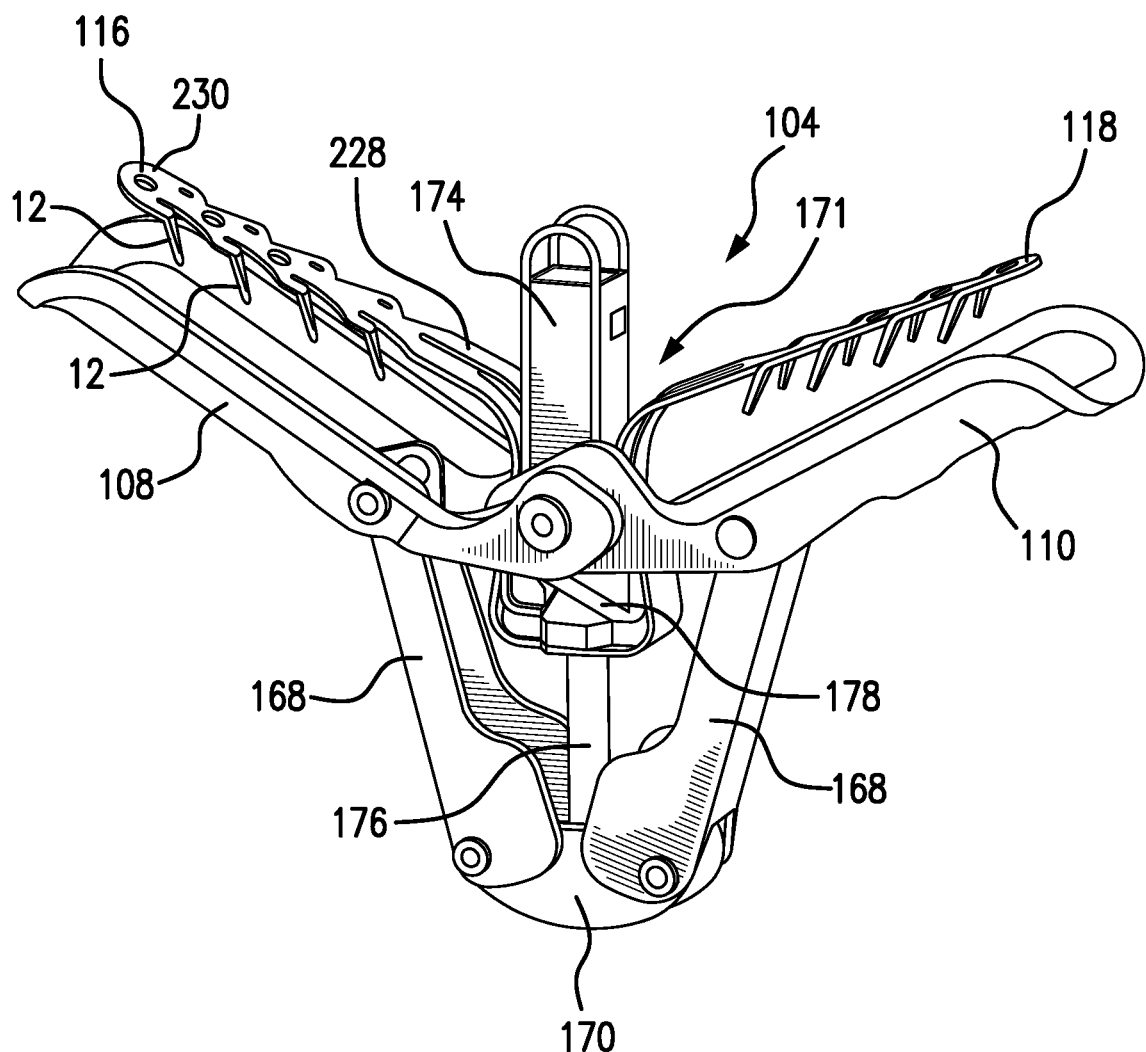
FIG. 1 is a perspective view of an exemplary embodiment of a fixation device for use in accordance with the disclosed subject matter.

Reference will now be made in detail to the various exemplary embodiments of the disclosed subject matter, exemplary embodiments of which are illustrated in the accompanying drawings.

The fixation device for use with the disclosed subject matter provides an edge-to-edge transcatheter valve repair option for patients having various conditions, including regurgitant mitral valves or tricuspid valves. Transcatheter (e.g., trans-septal) edge-to-edge valve repair has been established using a fixation device, such as the MitraClip Transcatheter Mitral Valve Repair device. These fixation devices generally are configured to capture and secure opposing native leaflets using two types of leaflet contacting elements. The first element is a sub-valvular arm (also known as a distal element or fixation element) to contact the ventricular side of a native leaflet to be grasped. With the arm positioned underneath to stabilize the native leaflet in a beating heart, a second gripping element (e.g., a proximal element) can be lowered or moved toward the arm and into contact with the atrial side of the native leaflet to capture the leaflet therebetween. Once each native leaflet is captured by a respective arm and gripping element, the fixation device can be closed by raising or moving the arms toward a center of the fixation device such that the leaflets are brought into coaptation, which results in a reduction in valvular regurgitation during ventricular systole. Furthermore, a covering can be provided on the arms and/or gripping elements to facilitate tissue ingrowth with the captured leaflets.

Additional details of exemplary fixation devices in accordance with the disclosed subject matter are set forth below. Furthermore, a number of patents and publications disclose additional details and aspects of such fixation devices and related operations. See for example, U.S. Pat. No. 7,226,467 to Lucatero et al.; U.S. Pat. No. 7,563,267 to Goldfarb et al.; U.S. Pat. No. 7,655,015 to Goldfarb et al.; U.S. Pat. No. 7,736,388 to Goldfarb et al.; U.S. Pat. No. 7,811,296 to Goldfarb et al.; U.S. Pat. No. 8,057,493 to Goldfarb et al.; U.S. Pat. No. 8,303,608 to Goldfarb et al.; U.S. Pat. No. 8,500,761 to Goldfarb et al.; U.S. Pat. No. 8,734,505 to Goldfarb et al.; U.S. Pat. No. 8,740,920 to Goldfarb et al.; U.S. Pat. No. 9,510,829 to Goldfarb et al.; U.S. Pat. No. 7,635,329 to Goldfarb et al.; U.S. Patent Application Publication No. 2017/0042546 to Goldfarb et al.; U.S. Patent Application Publication No. 2017/0239048 to Goldfarb et al.; U.S. Patent Application Publication No. 2018/0325671 to Abunassar et al., the entirety of the contents of each of these patents and published applications is incorporated herein by reference.

In grasping tissue and leaflet capture for mitral valve disease, certain patient conditions and anatomies, such as those associated with larger dynamic gaps between leaflet tips, can create challenges for capture. As such, there is an opportunity for a fixation device capable of bridging larger gaps, such as in functional mitral regurgitation (FMR), while also providing more reliable leaflet capture, for example in cases of dynamic, chaotic, or overly severe degenerative mitral regurgitation (DMR), such as in cases of Barlow's Syndrome. Particularly, the size and configuration of the arm of the fixation device can significantly improve performance. However, such modifications can be configured to account for numerous factors to produce desired clinical benefit and still be deliverable transvascularly through a guide catheter. For example, a typical guide catheter size for delivery can have an inner diameter of about 0.22 inch or less. Furthermore, when positioned within a patient, the guide catheter defines a tortious path through which the fixation device can be delivered. As such, the fixation device can be configured to be capable of such delivery through the corresponding bends and turns of the guide catheter.

Additionally, and as previously noted, the fixation device can be configured to capture or grasp a leaflet between the arm and the gripping element. When in the closed position, it can facilitate further capture of adjacent leaflets positioned between two arms in the final implanted condition. Such capture can be a function of a contact patch area of the leaflets as defined by the width and configuration of the arms. Hence, increasing arm width along select lengths of the arm can increase contact patch area and corresponding capture. Additionally, arms can be configured with flexibility to increase deliverability through the guide catheter. In this manner, and in accordance with the disclosed subject matter, the arms can include a deformable frame creating a desired deformed lateral cross-dimension for delivery and a suitable undeformed width and configuration to provide a desired contact patch area.

Generally, and as set forth in greater detail below, the disclosed subject matter provided herein includes a fixation device for fixation of leaflets of a heart valve including a central assembly and at least one arm moveably coupled relative to the central assembly. The at least one arm includes a deformable frame having a first end and a second end and a longitudinal axis defined therebetween, the second end being moveable between a closed position and an open position. The deformable frame further includes first and second deformable flex portions, each flex portion extending along a respective lateral side of the deformable frame and having a deformed condition and an undeformed condition, and each flex portion having an outer lateral edge. The at least one arm has a maximum deformed arm lateral cross-dimension with the flex portions in the deformed condition and a maximum undeformed arm width defined between the outer lateral edge of the first flex portion and the outer lateral edge of the second flex portion in the undeformed condition. The ratio of the maximum deformed arm lateral cross-dimension to the maximum undeformed arm width is at least 1:1.3. The fixation device further includes at least one gripping element moveable relative to the at least one arm to capture a native leaflet therebetween.

Figure 2A:
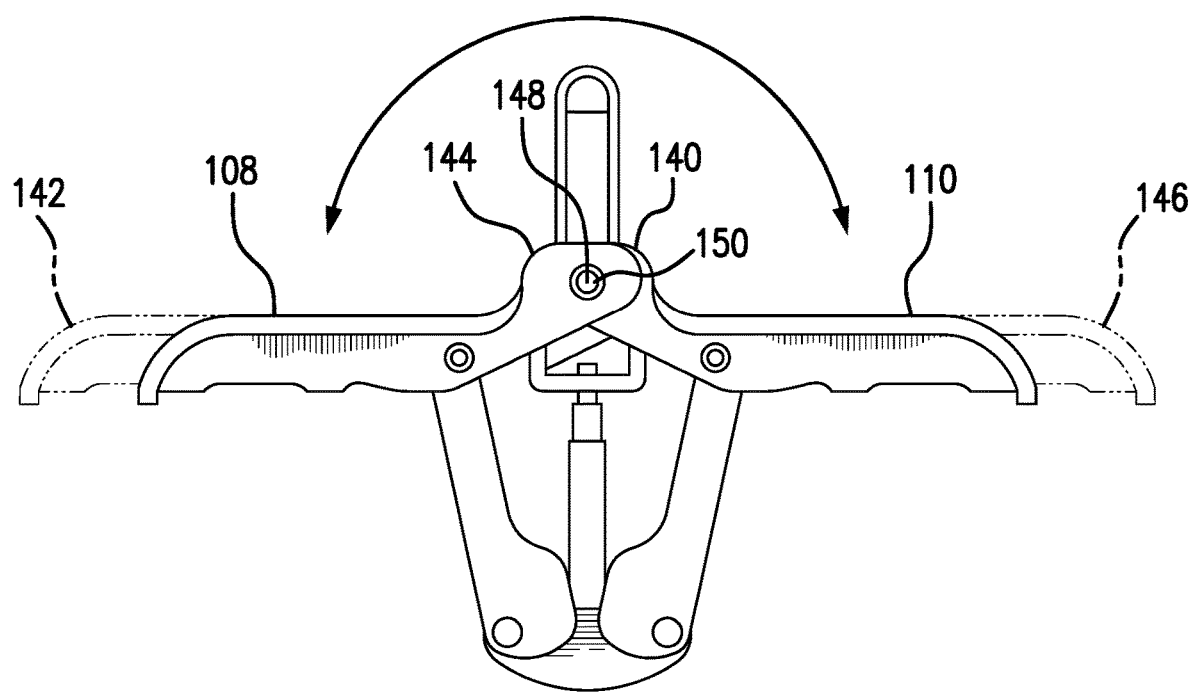
FIG. 2A is a front view of the fixation device of FIG. 1, wherein optional arms of greater length are depicted with dashed lines.

Referring to FIGS. 1-2A for the purpose of illustration and not limitation, a fixation device 104 for fixation of native leaflets of a heart valve is disclosed herein. The fixation device as embodied herein includes a central assembly 171. The central assembly 171 can include various central components for operation and release of the fixation device, for example, a coupling member 174 as described further in the disclosures of the patents and applications incorporated in their entirety by reference herein. The fixation device as depicted further includes at least one arm 108 moveably coupled relative to the central assembly 171. As shown, the fixation device can further include a second arm 110 moveably coupled relative to the central assembly 171. For purpose of understanding and reference only, FIGS. 1, 2A-2D and 3A-3B depict the arms without the flex portions of the disclosed subject matter.

With reference to FIG. 2A, for illustration and not limitation, each arm 108, 110 can be rotatable or moved about a respective axis point 148, 150 between closed, open and inverted positions, as well as any position therebetween. Furthermore, the arms 108, 110 can be selected from a range of suitable lengths, wherein the appropriate length can be selected by the physician or health care provider after inspection of a patient. For purpose of comparison, a first length of each arm 108, 110 is depicted in FIG. 2A in solid lines, and a second longer length of each arm of the disclosed subject matter is depicted in dashed lines. Each arm depicted in solid lines can be an entirely separate arm with a different length as compared to the corresponding arm depicted in dashed lines.

Figure 2B:
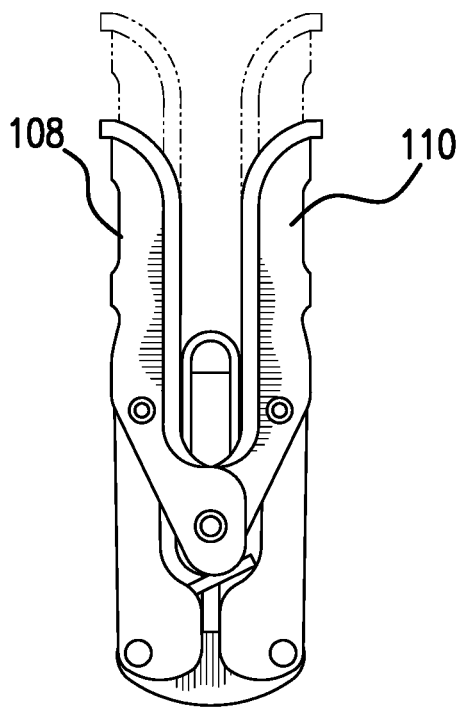
FIGS. 2B-2D are front views of the fixation device of FIG. 1 at various positions, wherein optional arms of greater length are depicted with dashed lines.
Figure 2C:
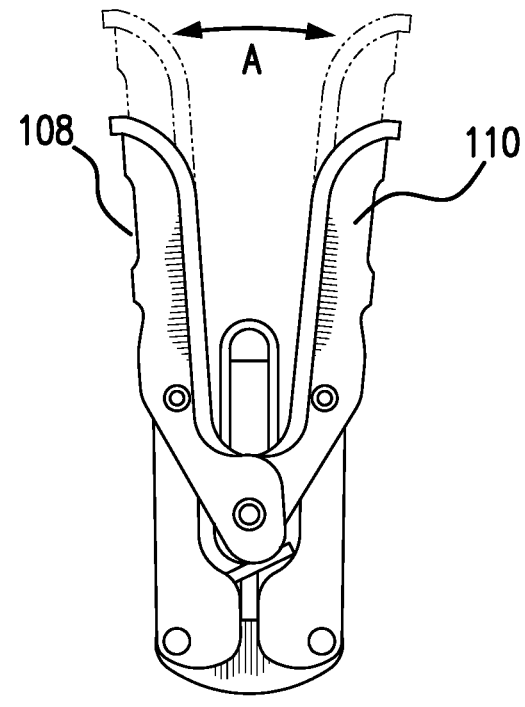
Figure 2D:
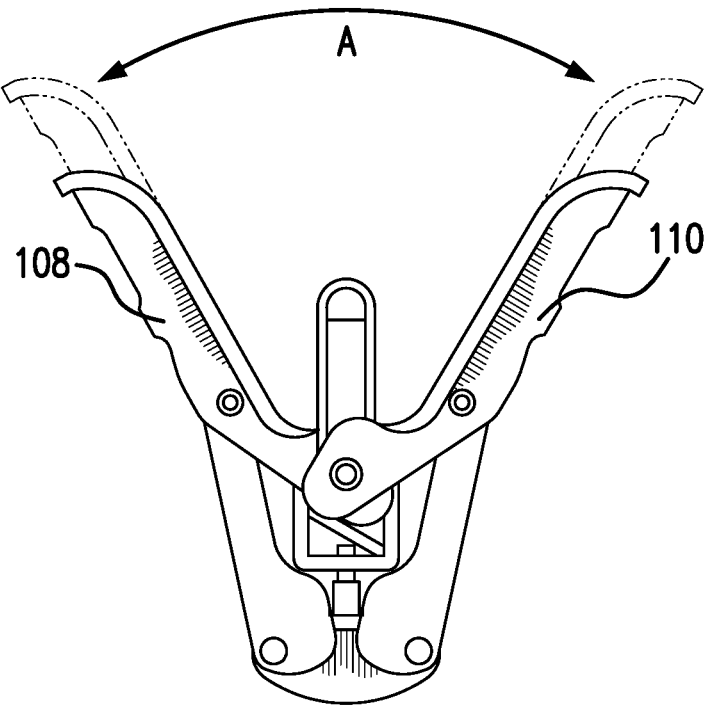

As depicted herein in FIGS. 2B-2D, various positions of the fixation device 104 are depicted for purpose of illustration and not limitation. Arms of longer length are illustrated in dashed lines for comparison to shorter arms. In FIG. 2B, the fixation device is in the closed position, wherein the arms are positioned axially in alignment, e.g., vertically or nearly vertically as shown. FIGS. 2C and 2D illustrate the arms positioned with an angle A between each other. In FIG. 2C, angle A is about 10 degrees and in FIG. 2D angle A is about 60 degrees. As disclosed herein, the fixation device is in the closed position when angle A is about 30 degrees or less, although another angle may result when leaflets of greater thickness are captured therebetween. Although not depicted, the arms can continue to open until angle A exceeds 180 degrees, e.g., inverted.

Figure 3A:
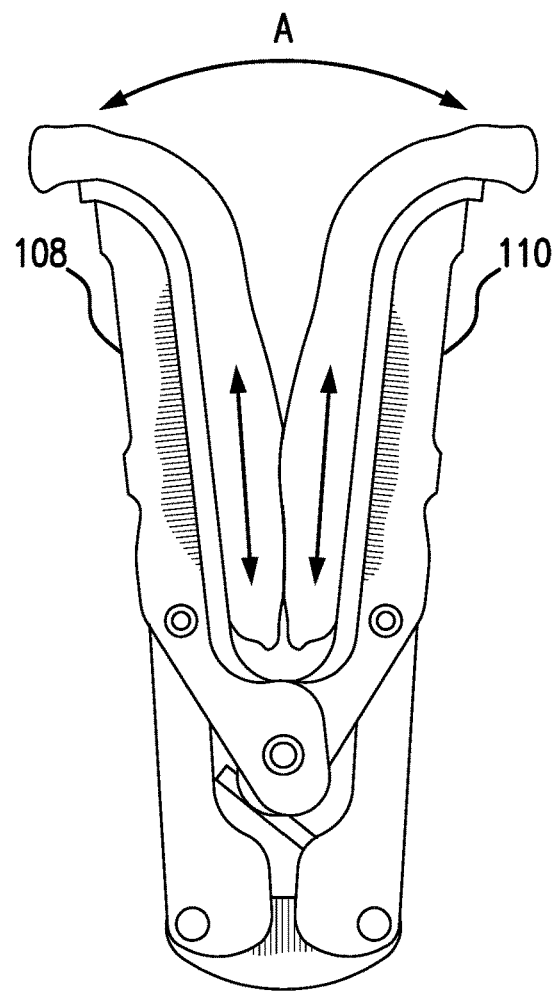
FIG. 3A is a front schematic view of the fixation device of FIG. 1 having leaflets captured therein.
Figure 3B:
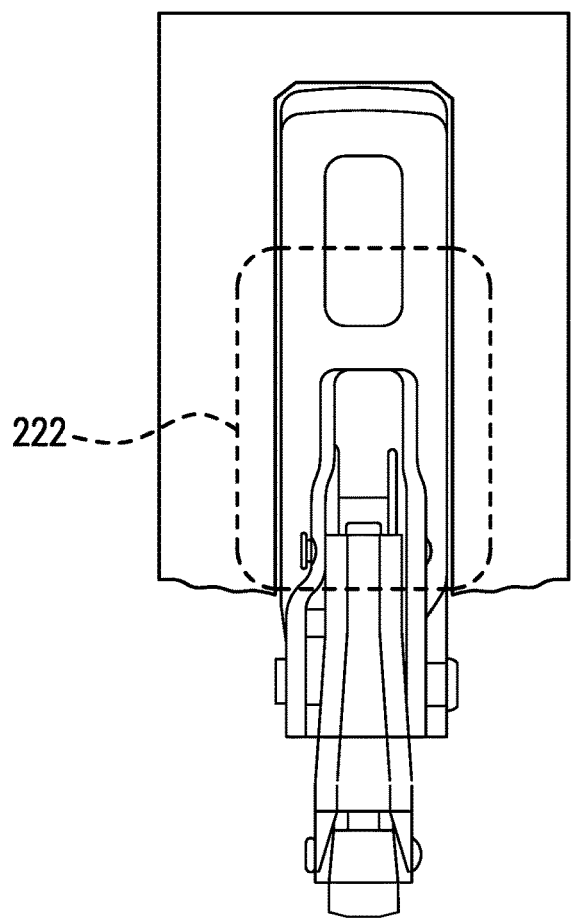
FIG. 3B is a side view of the fixation device of FIG. 1 to schematically depict a contact patch area.

As previously noted generally, and as set forth in further detail below, a native leaflet can be captured between each arm and a respective gripping element. Each arm can then be moved toward its closed position. In this manner, adjacent leaflets can further be captured between two arms in the closed position. For example, and for illustration only, FIGS. 3A-3B show the fixation device 104 depicted with the arms 108, 110 at an angle A of about 20 to 30 degrees with two leaflets captured therebetween, wherein each leaflet is captured between an arm and a respective gripping element (wherein gripping element is not shown for clarity). As illustrated in FIG. 3B, a contact patch 222 depicted in dashed lines is defined by the area of tissue contact between the arms. The contact patch area 222 represents a tissue-to-tissue contact patch area defined by the area of a leaflet in contact with a counterpart leaflet. As previously noted, FIG. 3B depicts a representative contact patch area when each arm does not include flex portions and the arms of the fixation device are at an angle A of about 20 to 30 degrees. The angle A can affect the contact patch area 222 wherein a reduced angle A can increase the contact patch area 222, and likewise an increased angle A can decrease the contact patch area 222.

In accordance with the disclosed subject matter, an arm configuration is provided with a deformable frame having deformable flex portions to increase contact patch area and capture of adjacent leaflets between two arms of the fixation device in a closed or final implanted position. Additionally, each arm can be configured to space the contact patch area from the first end of the arm, such as intermediate along the length of the arm or proximate the second end of the arm. Furthermore, the deformable frame has a deformed condition for delivery, and an undeformed condition for final implantation. A deformable frame of an arm can be made of shape memory material, e.g., Nitinol, or other sufficiently flexible material capable of being distorted when the deformable frame is in the deformed condition.

Figure 4:
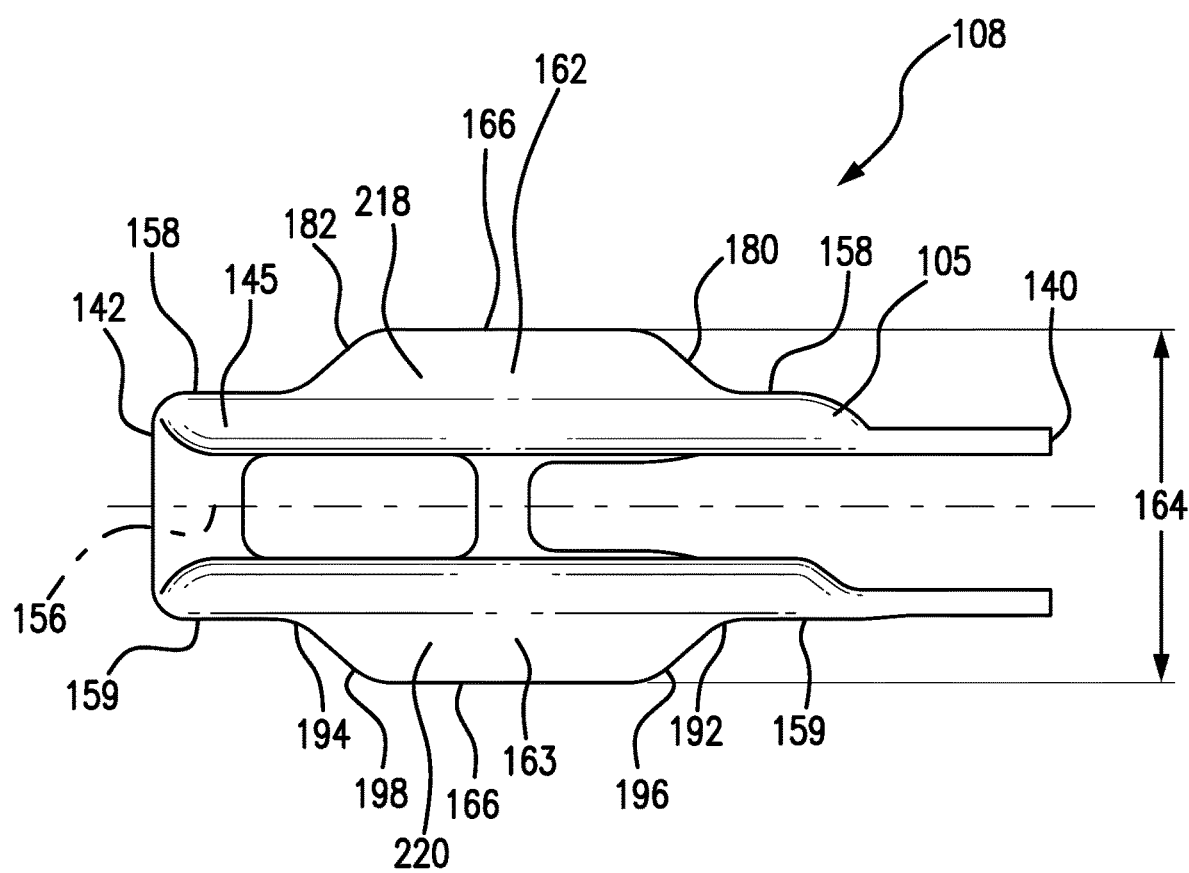
FIG. 4 is a plan view of an exemplary embodiment of a deformable frame of an arm in an undeformed condition in accordance with the disclosed subject matter.

For purpose of illustration and not limitation, a plan view of an arm comprising a deformable frame for a fixation device in accordance with the disclosed subject matter is depicted in FIG. 4. Although FIG. 4 and other figures throughout this application only depict a single arm for clarity, it is understood that the various features of the at least one arm 108 can apply similarly to one or more additional arms, such as, the second arm 110. The at least one arm 108 is moveably coupled relative to the central assembly 171.

As shown in FIG. 4, the arm 108 of the disclosed subject matter comprises a deformable frame 105 having a first end 140 and a second end 142 and a longitudinal axis 156 defined therebetween. The deformable frame 105 comprises first and second deformable flex portions 218, 220. Each flex portion extends along a respective lateral side of the deformable frame 105 and has a deformed condition and an undeformed condition. Furthermore, each flex portion has an outer lateral edge 166. The at least one arm 108 has a maximum undeformed arm width 164 defined between the outer lateral edge 166 of the first flex portion 218 and the outer lateral edge 166 of the second flex portion 220 in the undeformed condition.

As disclosed herein, the flex portions can be provided with a variety of configurations to facilitate the deformed conditions of the arms. Furthermore, the deformable frame 105 of the discussed subject matter further comprises a trough 145 defined along the longitudinal axis 156 to receive a gripping element 116 as described herein. For example, and as embodied herein, the first flex portion 218 can comprise a deformable first wing extension 162 extending laterally from a first lateral side of the trough 158 and the second flex portion 220 can comprise a deformable second wing extension 163 extending laterally from a second lateral side of the trough 159. As depicted in FIG. 4, the first and second wing extension define a maximum undeformed arm width 164 between the outer lateral edges 166 of each wing extension 162, 163 in the undeformed condition. For purpose of delivery, each wing extension can be deformed such as by folding or curling each wing extension along the respective lateral side of the trough so as to substantially resemble the profile and configuration such as depicted in FIG. 3B. In this manner, the arm 108 in the deformed condition defines a maximum deformed arm lateral cross-dimension 165 with the flex portions 218, 220 in the deformed condition, which, as embodied herein, is generally equal to the lateral cross-dimension between the opposing lateral sides of the trough 145. For purpose and illustration and not limitation, the deformable frame 105, including the trough 145 and the first and second wing extensions 162, 163, can be a single piece construction. Further, the first and second wing extensions 162, 163 can be made of a variety of different materials, including, for example, a shape memory material as described further below.

As embodied herein, and with reference to FIG. 4, the first and second wing extensions 162, 163 can each have a first end edge 180 and a second end edge 182, wherein the first end edge 180 can extend between a respective lateral side of the trough 158, 159 and an outer lateral edge 166. As depicted, the first end edge 180 can be located closer to or proximate a first end 140 of the trough 145. The second end edge 182 can extend between the respective lateral sides of the trough 158, 159 and the outer lateral edge 166. The second end edge can 182 be located closer to or proximate the second end 142 of the trough. With further reference to FIG. 4, the first end edge 180 can have a first end fillet 192 at an intersection with the respective lateral side of the trough 158, 159. Likewise, the second end edge 182 can have a second end fillet 194 at an intersection with the respective lateral side of the trough 158, 159. Additionally, and as further depicted for illustration and not limitation, the first end edge 180 can have a first end round 196 at an intersection with the outer lateral edge 158. Likewise, the second end edge 182 can have a second end round 198 at an intersection with the outer lateral edge 166. The wing extensions depicted in FIG. 4 are intended for purpose of illustration and not limitation, and wing extensions having various other configurations and dimensions are contemplated.

As previously noted, and in accordance with the disclosed subject matter, the fixation device 104 further includes at least one gripping element 116, for example as shown in FIG. 1. The gripping element 116 can be moveable relative to the at least one arm 108 to capture a second native leaflet therebetween. In particular, the at least one gripping element 116 has a first end 228 coupled to a portion of the fixation device and a second end 230 moveable relative to the at least one arm 108. In accordance with the disclosed subject matter, each arm can be configured to define or have a trough 145 aligned along the longitudinal axis 156. The trough can be configured to receive the gripping element 116 therein.

As embodied herein, each gripping element includes a plurality of friction elements 152, such as in rows. For example, each gripping element 116, 118 can have at least four rows of friction elements 152. The friction elements 152 can allow for improved tissue engagement during leaflet capture. If the fixation device requires adjustment after an initial leaflet capture, the arms can be opened, the gripping element can be raised vertically, and tissue can disengage from the fixation device, facilitating re-grasp and capture.

For example, and with reference again to FIG. 1, and as further embodied herein, each gripping element 116, 118 can be biased toward each respective arm 108, 110. Prior to leaflet capture, each gripping element 116, 118 can be moved inwardly toward a longitudinal center of the device (i.e., away from each respective arm 108, 110) and held with the aid of one or more gripping element lines (not shown) which can be in the form of sutures, wires, rods, cables, polymeric lines, or other suitable structures. The gripping line elements can be operatively connected with the gripping elements 116, 118 in a variety of ways, such as by being threaded through loops (not shown) disposed on the gripping elements 116, 118.

Figure 5:
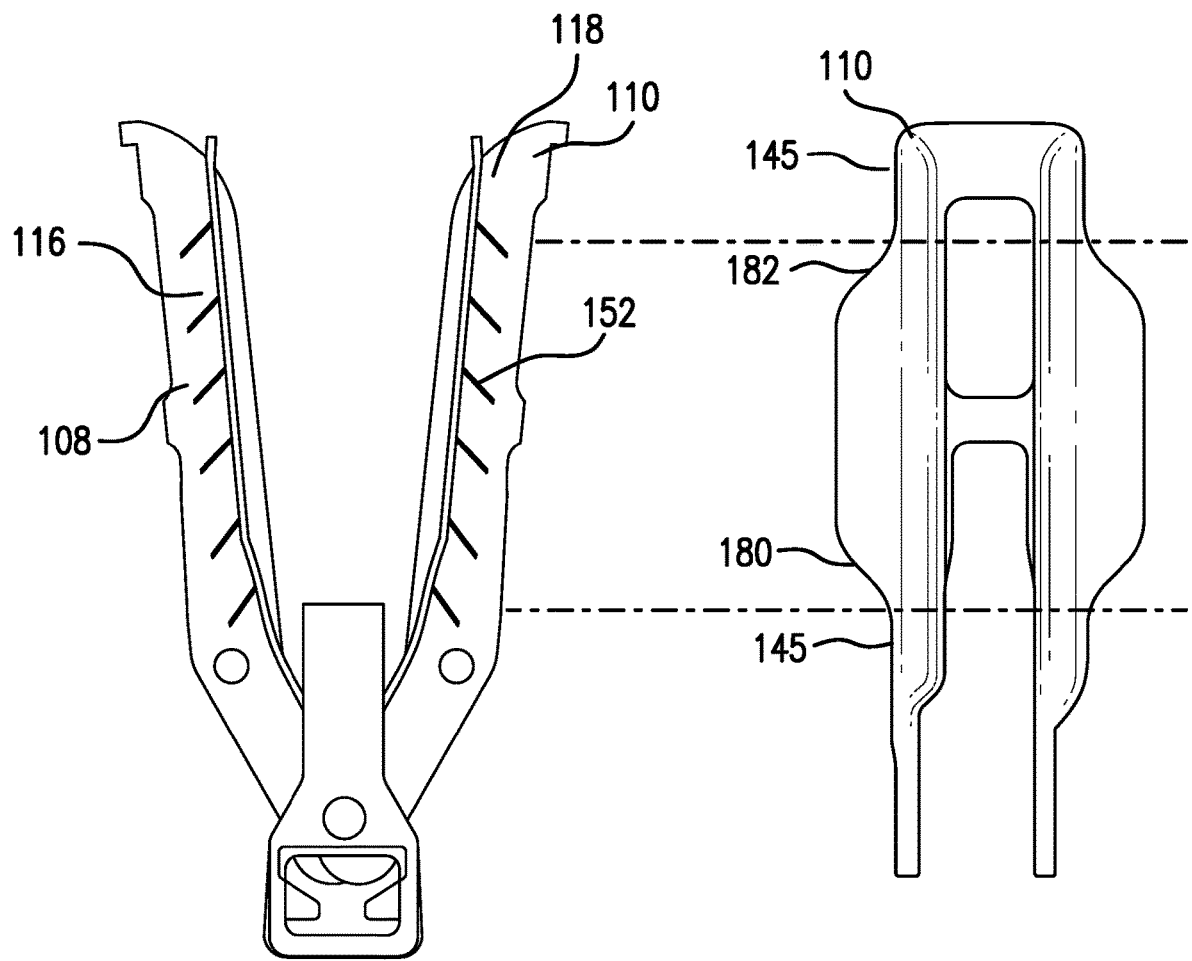
FIG. 5 is a front cross-section view of a portion of the fixation device of FIG. 1 aligned with a plan view of a corresponding deformable frame of the arm of the disclosed subject matter.

As previously noted, and as shown in FIG. 5, the at least one gripping element 116 can have a plurality of friction elements 152 along the length thereof. In accordance with another aspect of the disclosed subject matter, the arm and respective gripping element can be aligned such that when the at least one gripping element 116 is received within the trough of the at least one arm 108, the plurality of friction elements 152 are disposed along a length defined between the intersection of the first end edge 180 and the respective lateral sides of the trough 158, 159 at one end, and the intersection of the second end edge 182 and the respective sides of the trough 158, 159 of the respective wing extensions at the other end. Such a configuration can further increase the leaflet tissue securement at the region of flex portions, e.g., the wing extensions. In the configuration embodied herein, frictional elements positioned at the first and second ends of each wing extension can reduce or eliminate tissue erosion by more secure engagement at the desired locations.

Figure 6A:
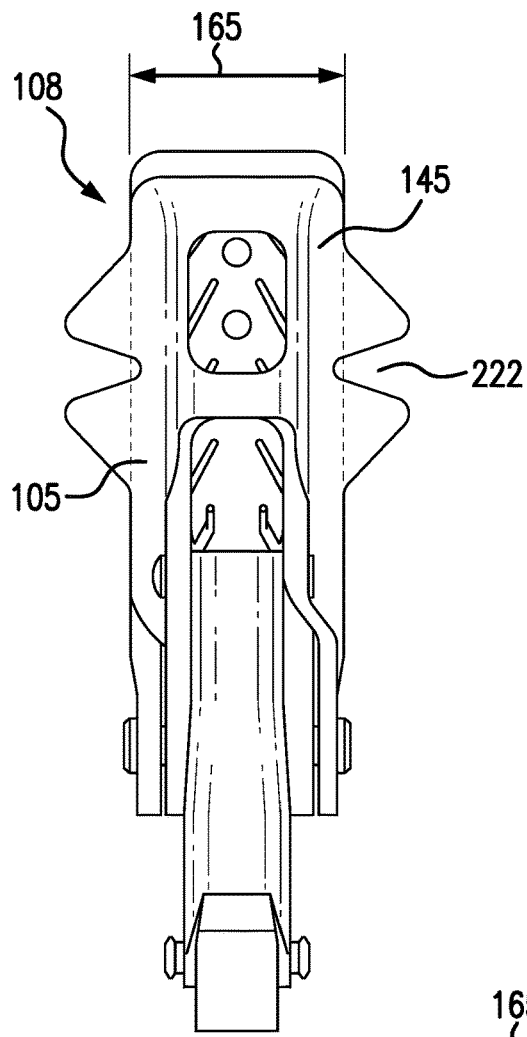
FIGS. 6A-6C are side views of a portion of the fixation device of FIG. 1, each with an alternative embodiment of the deformable frame of an arm in an undeformed condition in accordance with the disclosed subject matter.
Figure 6B:
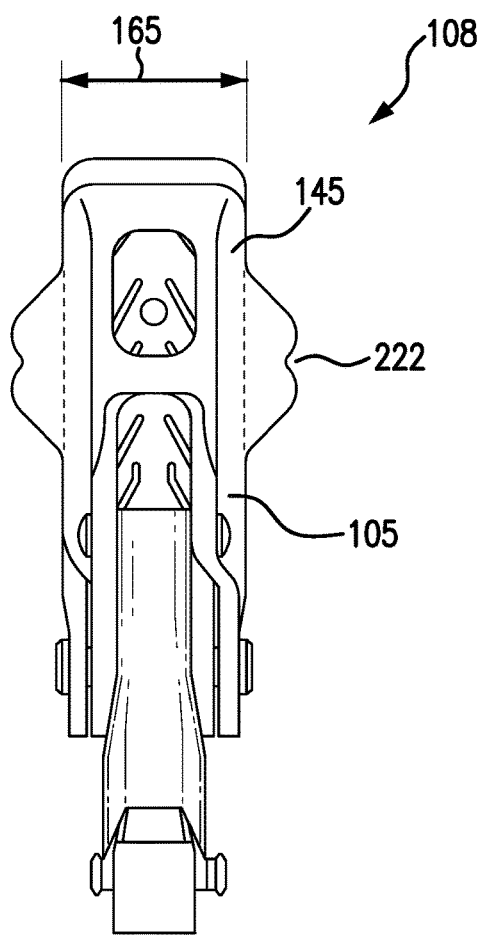
Figure 6C:
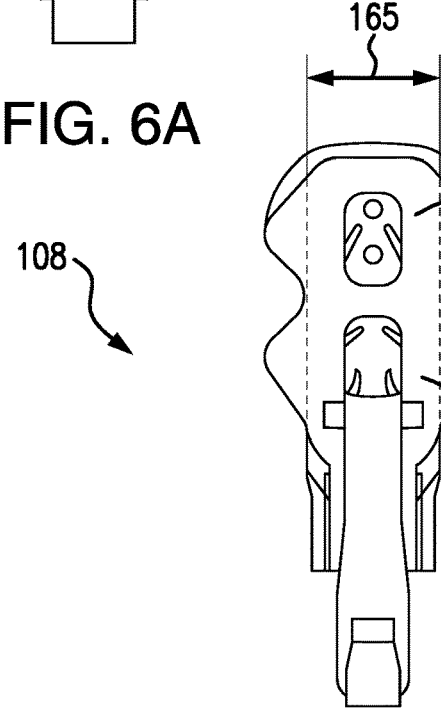

The size, shape and construction of the arm of the discussed subject matter can be varied or selected as desired to accommodate performance criteria. For example, and not by limitation, various frames of alternative arm configurations having flex portions comprising wing extensions in accordance with the discussed subject matter are disclosed herein. The configuration of the frame 105 can be selected to provide the desired performance of each arm (e.g., to capture and retain a leaflet, to track through and retract into a guide catheter, etc.). For example, as compared to the configuration of the wing extensions in FIG. 4, the first and second wing extensions 162, 163 disclosed in FIGS. 6A-6C each further includes at least one notch 222 defined along a respective lateral edge thereof to increase flexibility of the wing extensions. As depicted herein, wing extensions having a notch can include first and second end rounds 194, 198 that extend from the first and second end edges 180, 182, respectively, until the outer lateral edge 166 extends towards the longitudinal axis of the arm. As depicted in FIGS. 6A and 6C, the notch 222 can extend up to or into the trough 145. Alternatively, and as depicted in FIG. 6B, the notch 222 can terminate prior to the trough 145. Further, the various of the wing extensions can vary, as depicted, for example, wherein the first and second end rounds are relatively large in FIGS. 6B and 6C, and, by comparison, relatively small in FIG. 6A. The undeformed arm width at the innermost point of the notch (i.e., the deepest point of the notch) can be between about 25% and 50% less than the maximum undeformed arm width 164. For example, the maximum undeformed arm width 164 can be about 0.20 inch and the undeformed arm width at the innermost point of the notch can be between about 0.010 inch and 0.15 inch. Likewise, the maximum undeformed arm width 164 can be about 0.40 inch and the undeformed arm width at the innermost point of the notch can be between about 0.020 inch and 0.25 inch.

Figure 7A:
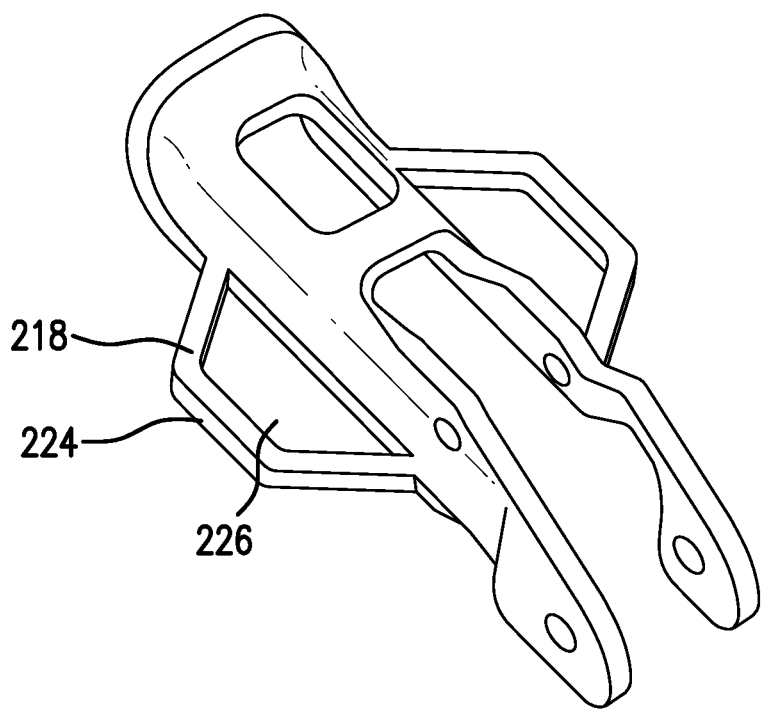
FIGS. 7A-7B are a perspective views of different embodiments of the deformable frames of arms in an undeformed condition in accordance with the disclosed subject matter.
Figure 7B:
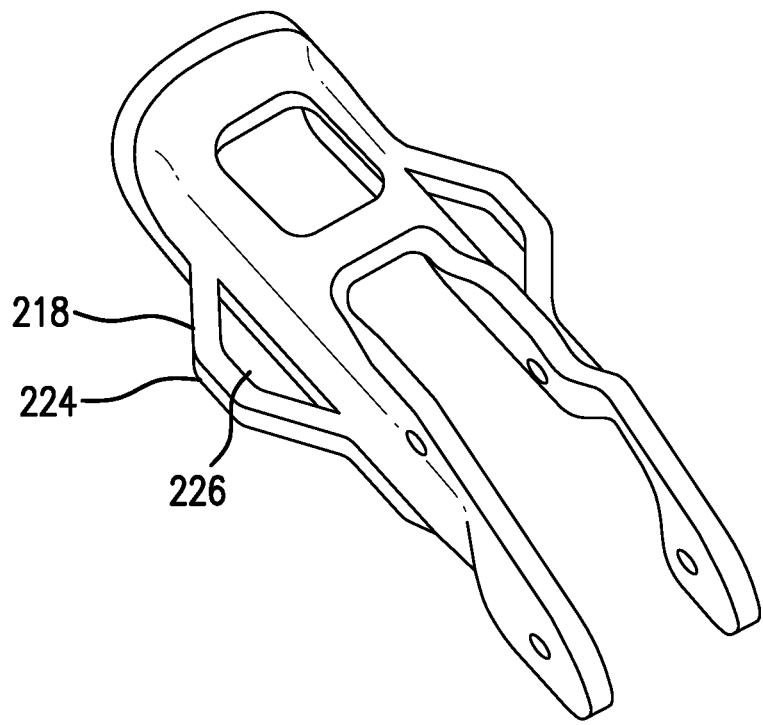

Referring to FIGS. 7A-7B, alternative embodiments of wing extension are disclosed, wherein the first and second wing extensions 162, 163 each comprises an open wing extension frame 224 defining a wing opening 226 therethrough in plan view. Although not shown, each wing extension embodiment disclosed herein can alternative be configured as an open wing extension frame. In this manner, and in accordance with the disclosed subject matter, the open wing extension frame 224 can further increase the compressibility of the deformable frame 105.

Figure 8:
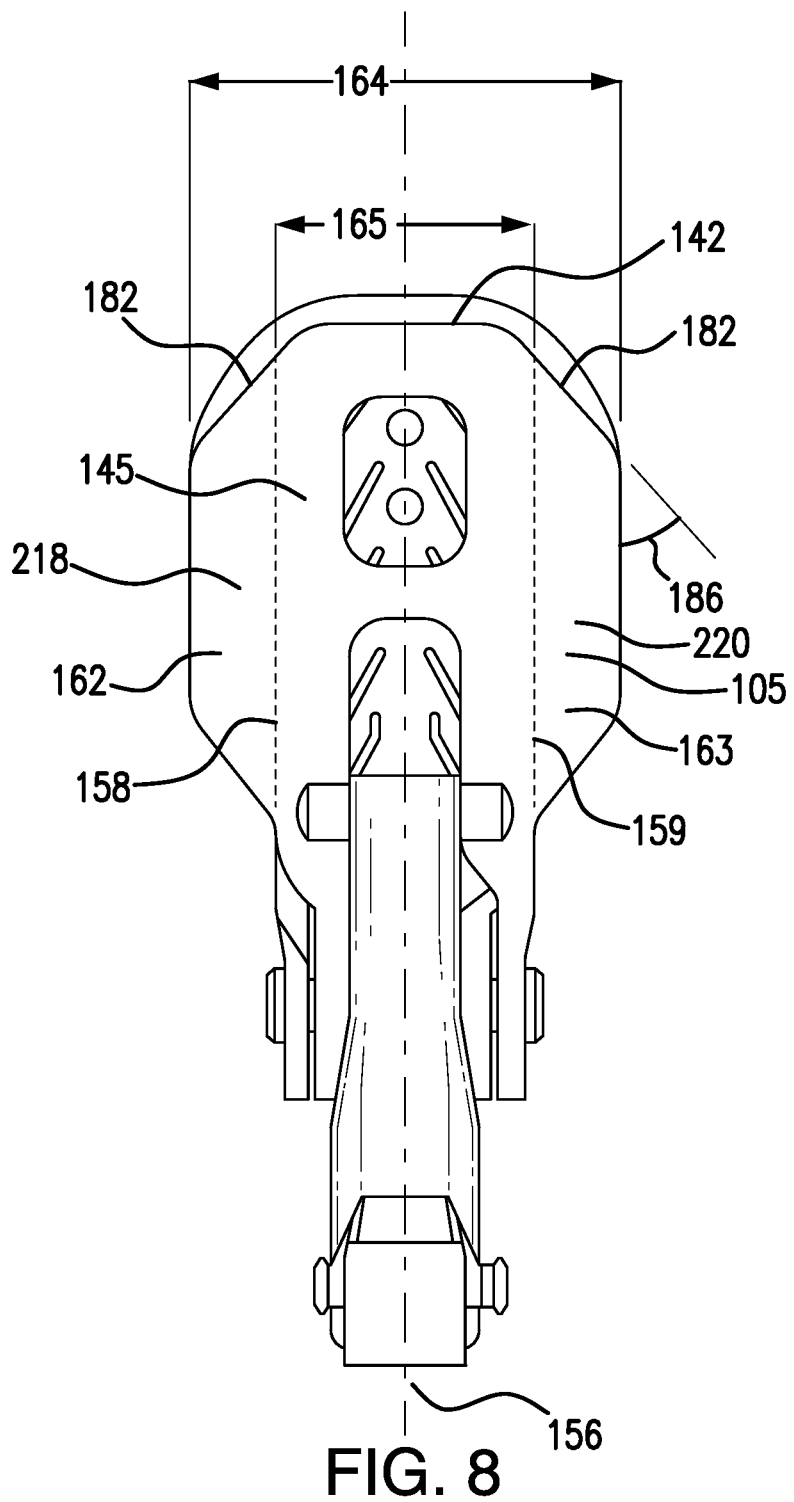
FIG. 8 is a side view of a portion of the fixation device of FIG. 1, with an exemplary embodiment of the deformable frame of the arm in an undeformed condition in accordance with the disclosed subject matter.

As further embodied herein in FIG. 8, an alternative arm configuration, referenced as a duck bill arm configuration, is disclosed for purpose of illustration and not limitation. In the duck bill arm configuration, first and second wing extensions 162, 163 each has a second end edge 182 extending laterally from the second end of the deformable frame 142 at a second end angle 186 defined between the second end edge 182 and the longitudinal axis 156. The second end angle 186 can be between 15 and 45 degrees. When undeformed and implanted, the second end angle forms a taper that that reduces undesirable focal stresses that may occur under various circumstances, e.g., with certain squared clip arms. Additionally, and as further embodied herein in FIG. 8, the maximum undeformed arm width 164 and corresponding contact patch area can be proximate the second end 142 of the deformable frame. For purpose of delivery, each wing extension 162, 163 can be deformed such as by folding or curling each wing extension along the opposing lateral sides 158, 159 of trough 145 so as to substantially resemble the profile and configuration such as depicted in FIG. 3B. In this manner, the deformable frame 105 of the arm in the deformed condition defines a maximum deformed arm lateral cross-dimension 165 with the flex portions 218, 220 in the deformed condition, which, as embodied herein, is generally equal to the lateral cross-dimension between the opposing lateral sides 158, 159 of the trough 145.

Figure 9:
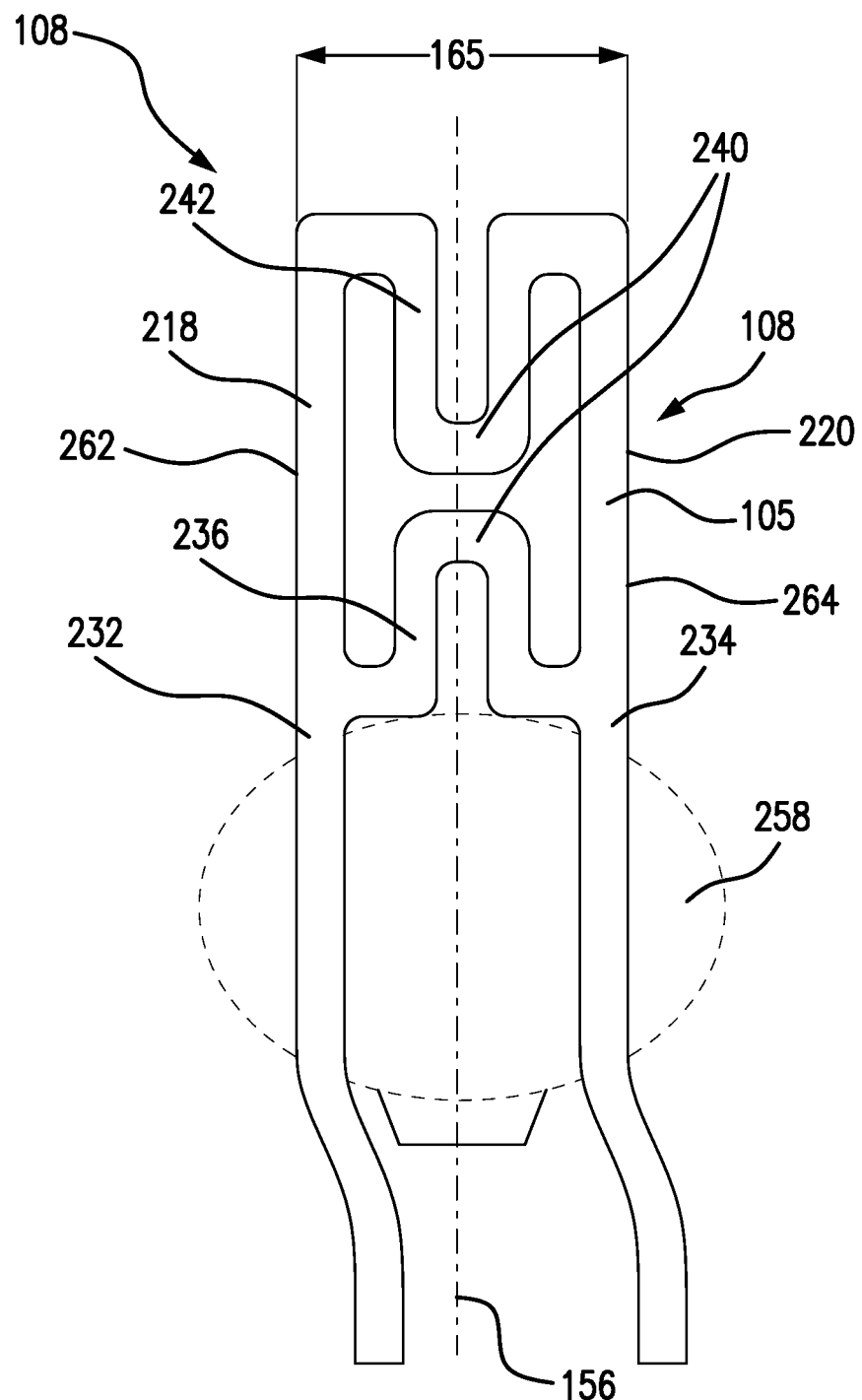
FIG. 9 is a schematic plan view of an alternative embodiment of a deformable frame of an arm in a deformed condition in accordance with the disclosed subject matter.

In accordance with another aspect of the disclosed subject matter, and with reference to FIG. 9 for purpose of illustration and not limitation, the first flex portion can include a deformable first flank member extending longitudinally along a first lateral side of the deformable frame. Likewise, the second flex portion can include a deformable second flank member extending longitudinally along a second lateral side of the deformable frame. The first and second flank members in the deformed condition can be aligned generally parallel with the longitudinal axis.

For example, and as embodied herein, the first flex portion 218 can comprise a deformable first flank member 232 extending longitudinally along a first lateral side of the deformable frame 262 and the second flex portion 220 can comprise a deformable second flank member 234 extending longitudinally along a second lateral side of the deformable frame 264. As shown in FIG. 9, the first and second flank members 232, 234 in the deformed condition being aligned generally parallel with longitudinal axis 156. As shown, for purpose of illustration and not limitation, the deformable frame 105 can include a first strut 236 extending laterally from the first flank member 232 to the second flank member 234. The first strut 236 can comprise a hinge portion 240 having a compressed configuration with the deformable frame 105 in the deformed condition, as shown for example in FIG. 9.

Additionally, and as further illustrated herein, the deformable frame 105 can comprise an end strut 242 extending laterally from the first flank member 232 to the second flank member 234 at the second end of the deformable frame 105. The end strut 242 can comprise a hinge portion 240 having a compressed configuration with the deformable frame 105 in the deformed condition and an extended configuration with the deformable frame 105 in the undeformed condition. As embodied herein, the first strut 236 can be spaced longitudinally from the end strut 242. To enable movement between the deformed and unformed conditions, the deformable frame, including the first and second flank members 232, 234 and struts 236, 242, can comprise shape memory material and bias toward the undeformed condition, and/or heat treated to expand toward the undeformed condition when a predetermined temperature is reached or exceeded. Although not shown, additional variations are contemplated, such as a deformable frame 105 having an end strut 242 and a hinge portion 240, wherein no additional strut (e.g., first strut 236) is included.

Figure 20:
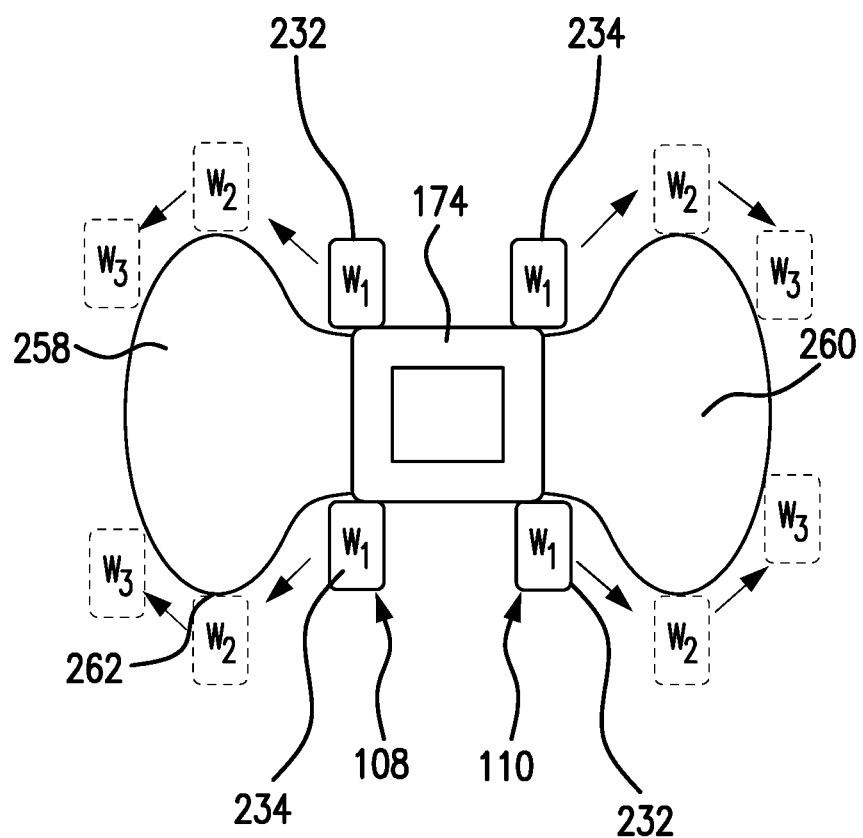
FIG. 20 is a schematic top view of an alternative embodiment of the fixation device of FIG. 1 having boss features.

In accordance with a further aspect of the disclosed subject matter, and with continued reference to FIG. 9 and further reference to FIG. 20, the fixation device 104 can include a first boss 258 (depicted schematically) corresponding to the first arm 108 and a second boss 260 corresponding to the second arm 110. Each of the first and second boss 258, 260 can have a tapered or curved geometry (e.g., a hemispherical shape). As embodied herein, for illustration and not limitation, the boss 258, 260 can be secured to the coupling member 174. As the arm 108, 110 moves towards the closed the position, the boss 258, 260 can be configured to engage and urge the first and second flank members 232, 234 outwardly towards the undeformed condition of the arm 108, 110. The boss 258, 260 can be disposed proximate the first end 140 of the arm and below tissue contact patch area 222 such that the boss can directly contact the flank members 232, 234. Alternatively, the boss 158, 160 can be disposed within the contact patch area 222 such that the boss 258, 260 is configured to engage the flank members 232, 234 with native leaflet tissue therebetween. Additional details of the boss 258, 260 are discussed below in FIG. 20.

Figure 10:
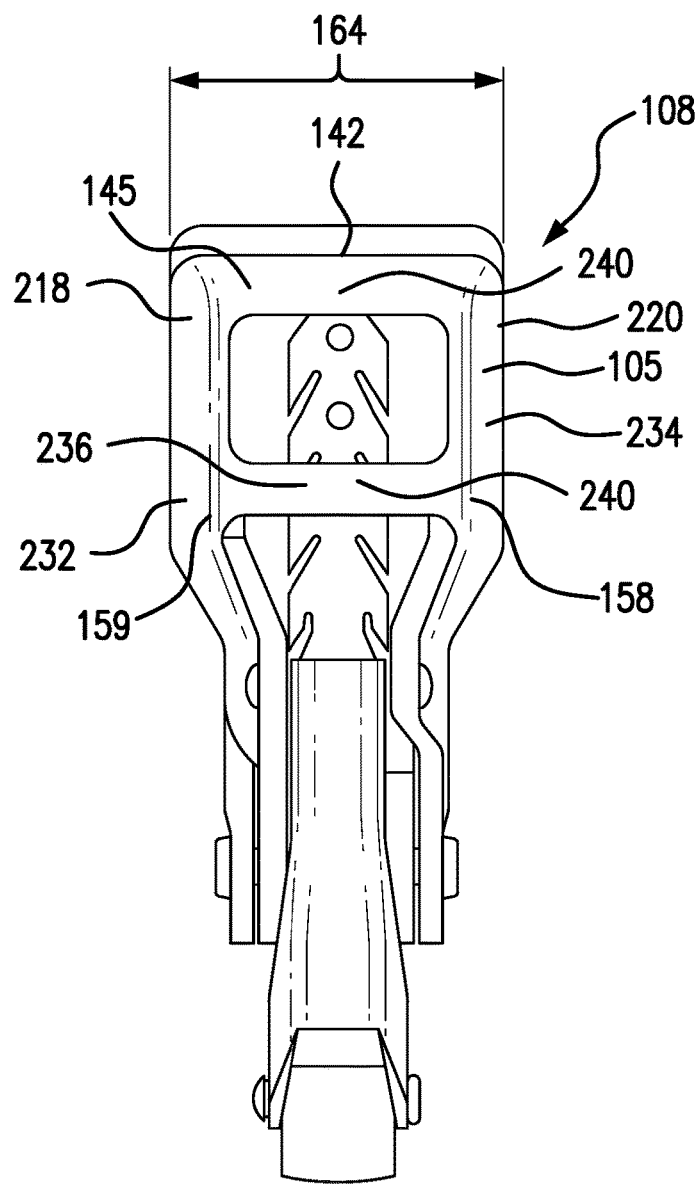
FIG. 10 is a side view of a portion of the fixation device of the FIG. 1, with an alternative embodiment of the deformable frame of the arm in an undeformed condition in accordance with the disclosed subject matter.
Figure 11:
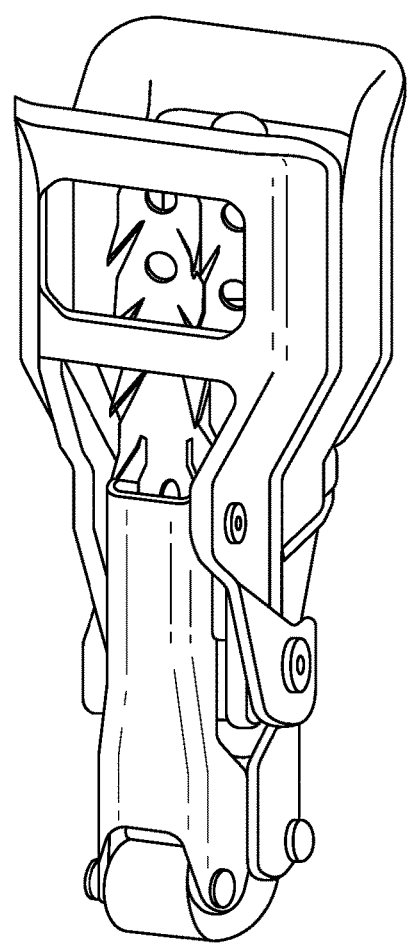
FIG. 11 is a perspective view of FIG. 10 including the alternative embodiment of the deformable frame of the arm.

Referring to FIGS. 10-11, the deformable frame 105 of the at least one arm 108, as previously shown schematically in FIG. 9 in the compressed or deformed condition for delivery, is now depicted in the expanded or released condition for implantation. As shown, the first strut 236 and the end strut 242 have an extended configuration with the deformable frame 105 of the arm 108 in the undeformed condition forming the maximum undeformed arm width 164. As embodied herein, the hinge portion 240 can be biased toward the extended condition. Additionally or alternatively, the flank members 232, 234 can be biased outwardly to the expanded or released condition.

Figure 12:
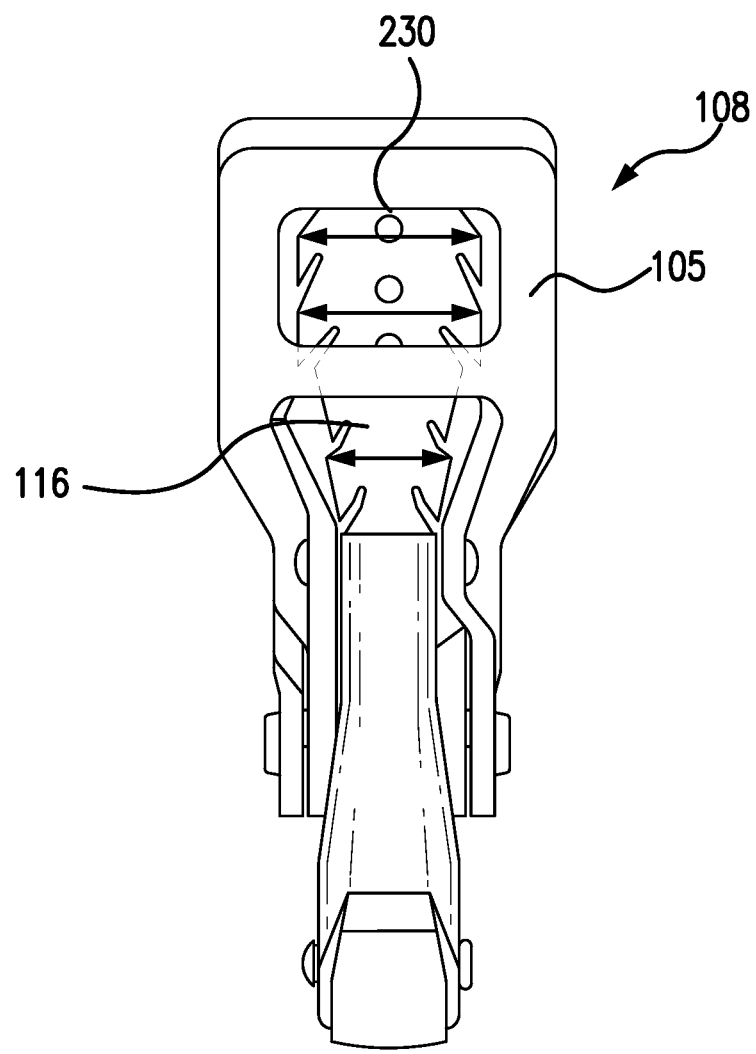
FIG. 12 is a side view of a portion of the fixation device of FIG. 1, with another exemplary embodiment of a deformable frame of an arm in an undeformed condition and a gripping element of the disclosed subject matter.

Although each of the embodiments of the FIGS. 4-8 depict an arm of the disclosed subject matter having a trough 145 of generally uniform width, it is understood alternative configurations can be provided. For example, and with continued reference to FIGS. 10 and 11, the arm of the disclosed subject matter can be provided with a trough 145 having a varied width along a length of the arm 108. In this manner, and in accordance with another aspect of the disclosed subject matter, the deformable frame 105 can include a trough 145 having a greater width between opposing lateral sides of the trough 158, 159 along a length of the arm 108 proximate the maximum undeformed arm width 164. With reference to the example embodiment of FIGS. 10-11, the maximum undeformed arm width 164 can be disposed proximate the second end 142 of the deformable frame 105, such as by providing wing extensions 218, 220 disposed proximate the second end 142. The trough 145 can be provided with an increasing width between lateral sides of the trough aligned accordingly. As such, the trough 145 in the undeformed condition can have width sized to receive the at least one gripping element 116 as depicted in FIGS. 10-11. With reference to FIG. 12, the gripping element, if made of suitable material, likewise can increase in width to correspond to the increasing width of the trough 145. That is, and as depicted in FIG. 12, the gripping element 116 can have a greater width proximate the second end 230 of the gripping element 116. The fixation device can further comprise a second gripping element 118 of similar configuration moveable relative to the second arm 110 to capture a native leaflet therebetween. Furthermore, if desired, although not shown, the second end edge of the wing extension 182 can be angled similar to the duck bill embodiment of FIG. 8.

Figure 13:
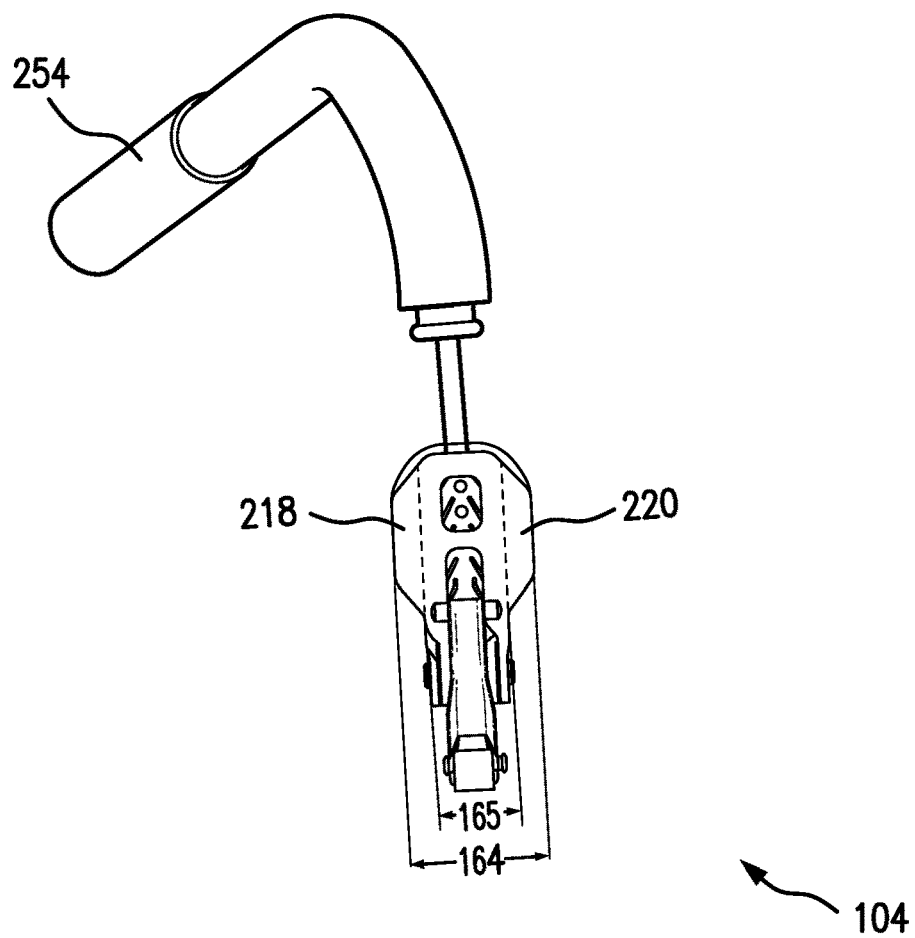
FIG. 13 is a perspective view of an exemplary embodiment of a distal end of a system for delivering the fixation device of FIG. 1.
Figure 14:
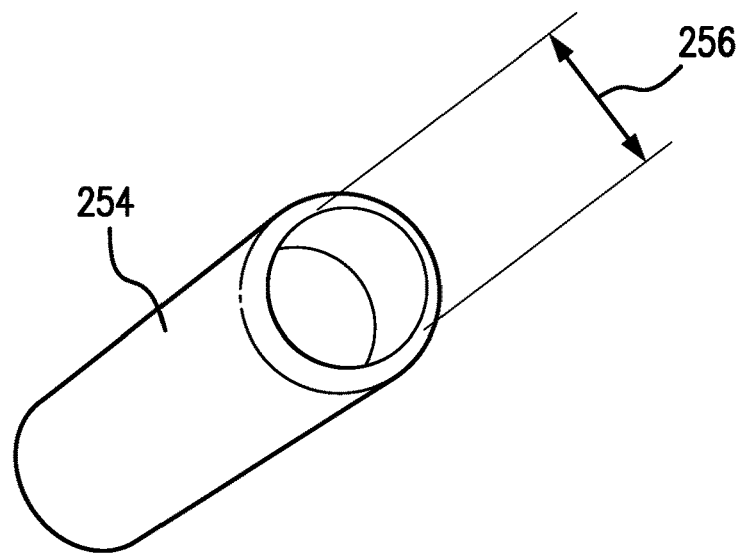
FIG. 14 is a perspective view of the distal end of the guide catheter in accordance with the delivery system of FIG. 13.

Referring now to FIGS. 13-14, a system for fixation of leaflets of a heart valve includes the fixation device 104 of the disclosed subject matter capable of delivery through a guide catheter 254 having an inner diameter 256, as shown for purpose of the illustration and not limitation. To facilitate delivery of the fixation device, the maximum deformed arm lateral cross-dimension 165 can be less than the inner diameter 256 of the guide catheter 254. To increase the contact patch area, as discussed above, the maximum undeformed arm width 164 thus can be greater than the inner diameter 256 of the guide catheter 254. That is the deformable frame 105 has a maximum deformed arm lateral cross-dimension 165 when the flex portions 218, 220 are in the deformed condition. Furthermore, the ratio of the maximum deformed arm lateral cross-dimension 165 to the maximum undeformed arm width 164, as discussed above, is at least 1:1.3, such as at least 1:1.5. For example, for a 16 French guide catheter, when the deformable frame 105 of the arm 108 depicted herein is delivered through the guide catheter, a maximum deformed arm lateral cross-dimension 164 can be between about 0.135 inch and 0.210 inch, such as a maximum deformed arm lateral cross-dimension 165 of about 0.203 inch. Each arm can have a variety of configurations to transition the arm from the deformed condition to the undeformed condition, such as, but not limited to, the various configurations disclosed herein.

With reference now to FIGS. 15-19, a variety of alternative configurations of the deformable frame having first and second flex portions comprising respective first and second flank members 232, 234 are also provided for purpose of illustration and not limitation. For example, in each of these embodiments, among others, the first flex portion 218 can comprise a deformable first flank member 232 extending longitudinally along a first lateral side of the deformable frame 105 and the second flex portion 220 can comprise a deformable second flank member 234 extending longitudinally along a second lateral side of the deformable frame 105. The first and second flank members 232, 234 in the deformed condition can be aligned generally parallel with longitudinal axis 156. As further embodied herein, the first and second flank members 232, 234 in the undeformed condition each can have at least a length thereof extending outwardly away from the longitudinal axis 156. See, for example, FIGS. 15B, 18B, 19B, and 20B.

Figure 15A:
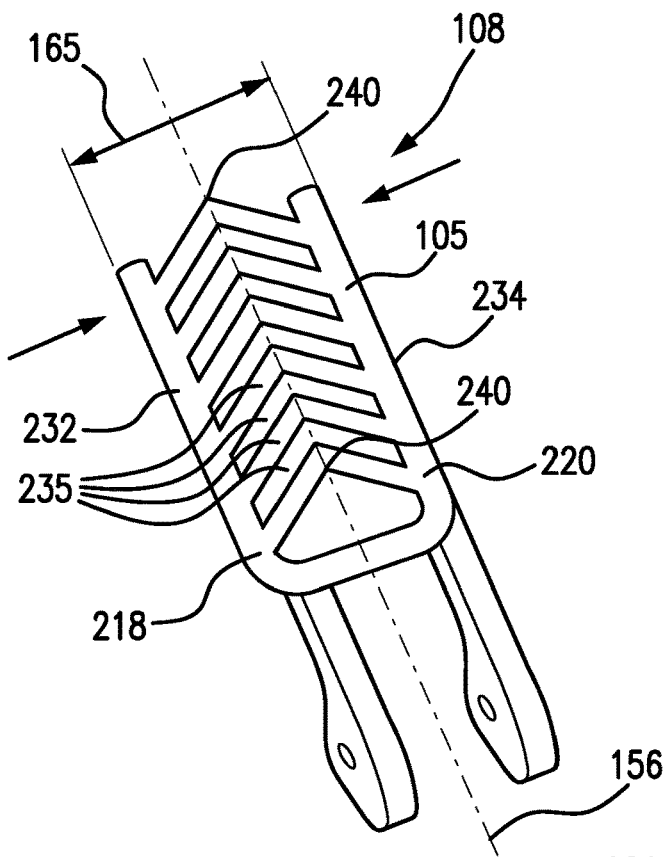
FIGS. 15A-15B are perspective views of an exemplary embodiment of a deformable frame of an arm in a deformed condition and an undeformed condition, respectively, in accordance with the disclosed subject matter.
Figure 15B:
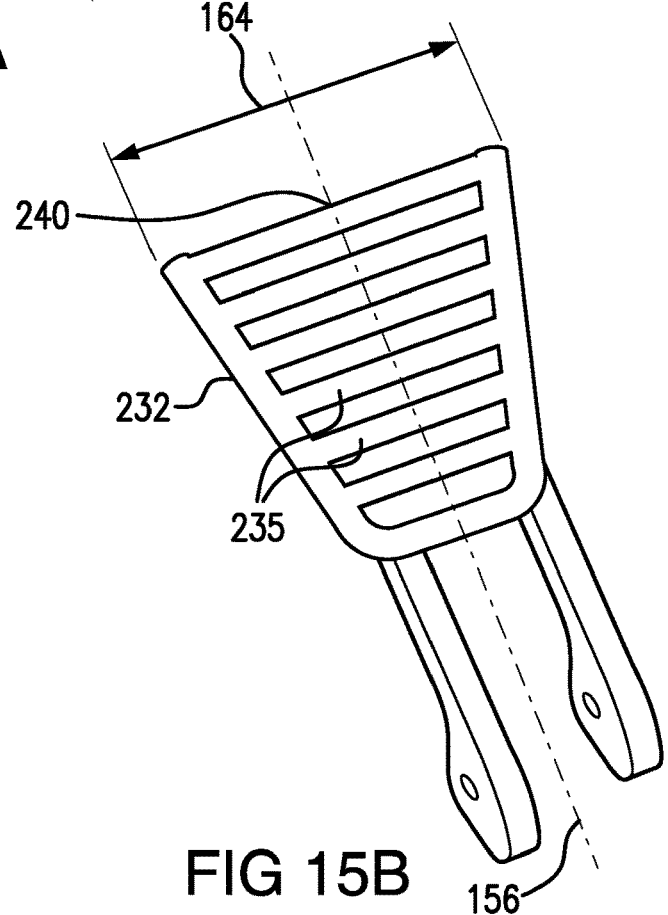

With reference now to the exemplary embodiment of FIGS. 15A-15B, the deformable frame 105 of the arm 108 includes a plurality of struts 235 extending laterally from the first flank member 232 to the second flank member 234. Each strut 235 includes a hinge portion 240 having a compressed configuration with the deformable frame 105 of the arm 108 in the deformed condition and an extended configuration with the deformable frame 105 of the arm 108 in the undeformed condition. For example, and as illustrated herein, each strut 235 has a generally V-shape in the deformed condition and a generally linear shape in the undeformed condition. As depicted herein in FIG. 15B, the V-shape struts 235 can be planar when the flank members extend outwardly. Struts having various other shapes are also contemplated. Further, the struts can be configured with a spring bias towards an expanded configuration, and/or configured to be manually activated towards the expanded configuration.

Figure 16A:
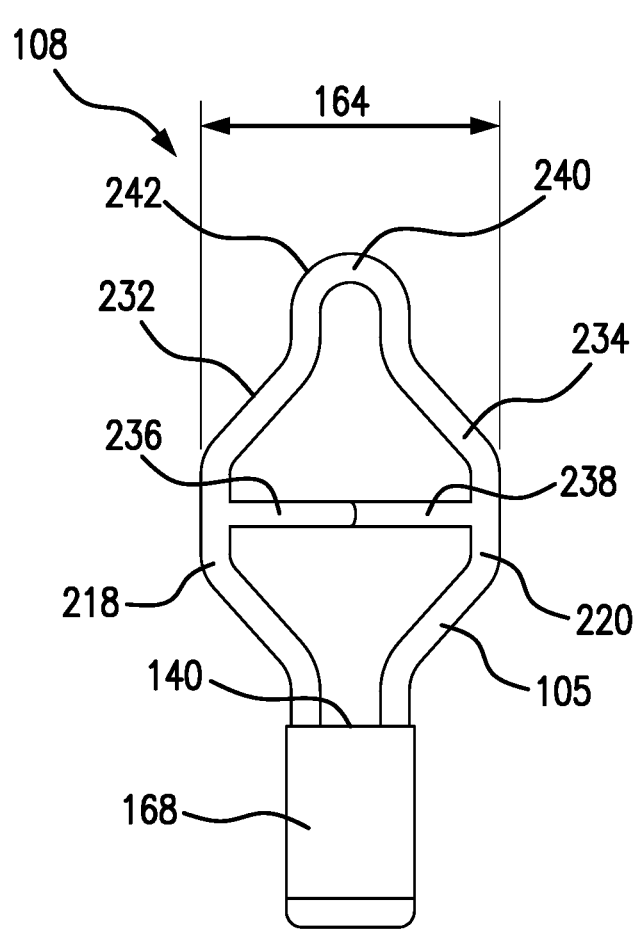
FIGS. 16A-16B are plan views of another embodiment of a deformable frame of an arm in a deformed condition and an undeformed condition, respectively, in accordance with the disclosed subject matter.
Figure 16B:
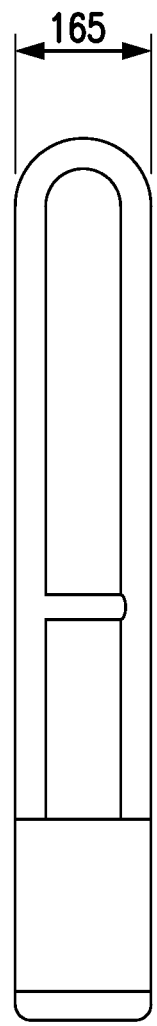

Further in accordance with the disclosed subject matter, and with reference to the embodiments disclosed in FIGS. 16A-16B, for purpose of illustration and not limitation, the deformable frame 105 can include a first strut 236 extending laterally from the first flank member 232 toward the second flank member 234 and a second strut 238 extending laterally from the second flank member 234 toward the first strut 236 member. As embodied herein, the first and second struts 236, 238 can be in an overlapping sliding arrangement for movement relative each other between the deformed condition and the undeformed condition. In this manner, the overlapping struts can provide structural stability along an intermediate section of the frame, yet still allow lateral expansion from the undeformed condition to the deformed condition. Additionally, and as previously discussed, the deformable frame 105 of the arm 108 embodied in FIGS. 16A-16B can further comprise an end strut 242 extending laterally from the first flank member 232 to the second flank member 234 at the second end of the deformable frame 105. Further, the end strut 242 disclosed herein includes a hinge portion 240 having a compressed configuration with the deformable frame 105 in the deformed condition, as shown in FIG. 16B, and an extended configuration with the deformable frame 105 in the undeformed condition, as shown in FIG. 16A.

Figure 17:
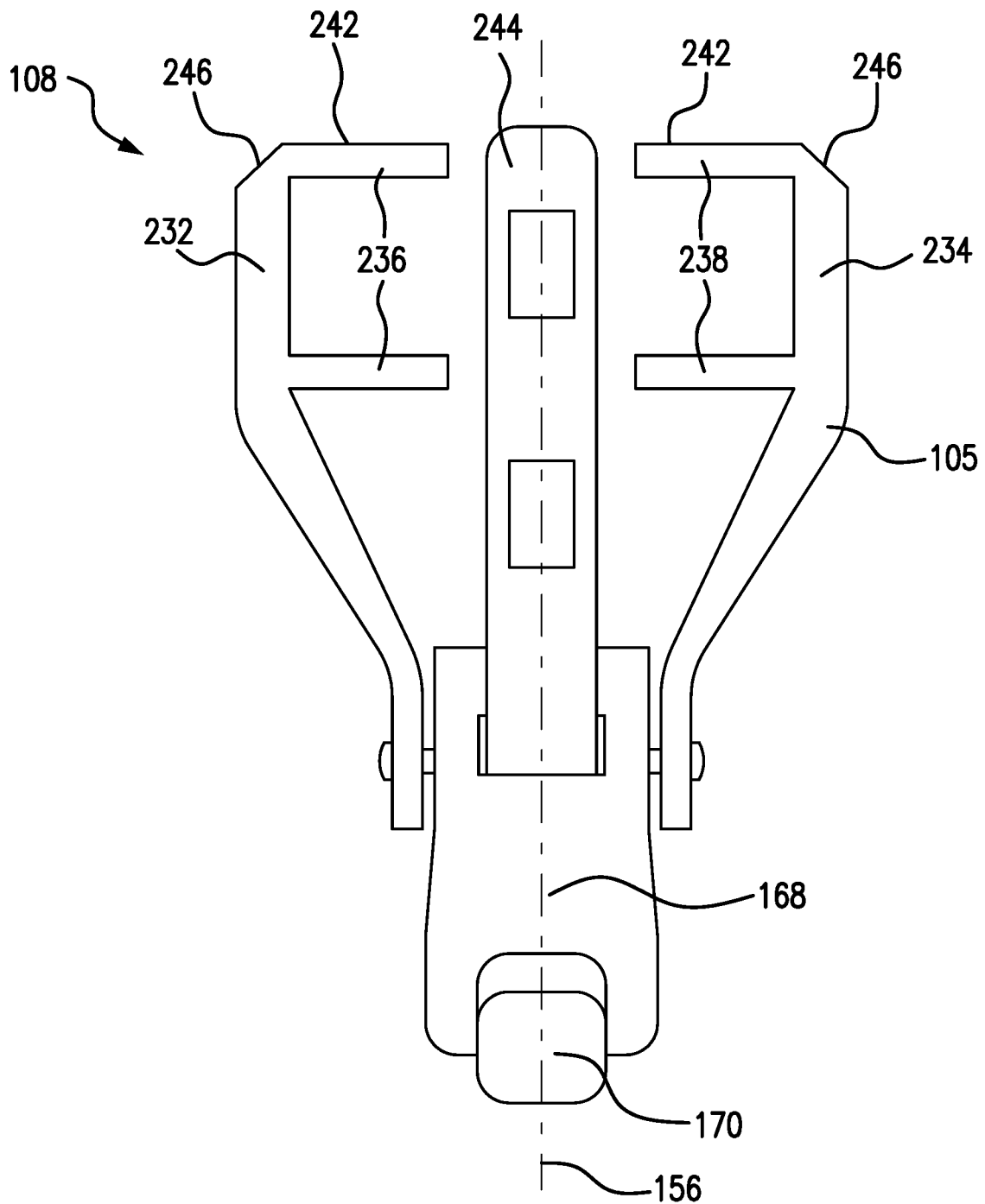
FIG. 17 is a side view of a portion of the fixation device of the FIG. 1, with an exemplary embodiment of another embodiment of deformable frame of an arm in an undeformed condition in accordance with the disclosed subject matter.

Alternatively, and as depicted in FIG. 17, the first and second struts 236, 238 can be laterally spaced from each other with the deformable frame 105 in the undeformed condition. Furthermore, and in lieu of a hinge, first and second struts 236, 238 can be configured to overlap at least in the deformed condition, not shown. As illustrated in FIG. 17, the arm 108 can include a middle support member 244 extending generally parallel with the longitudinal axis 156 between the first and second flank members 232, 234. Moreover, the first and second flank members 232, 234 each can have a tapered portion 246 proximate the second end of the deformable frame 105 for further strength and stability, as well to reduce undesirable focal stresses that may occur under various circumstances, e.g., with squared ends. Such a taper can likewise be produced with alternative frame configurations.

Figure 18A:
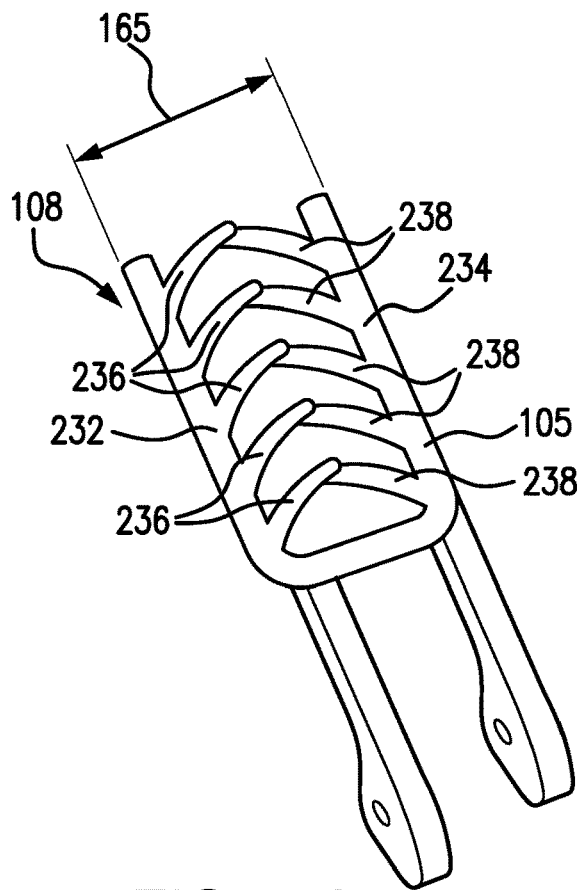
FIGS. 18A-18B are perspective views of an alternative embodiment of deformable frame of an arm in a deformed condition and an undeformed condition, respectively, in accordance with the disclosed subject matter.
Figure 18B:
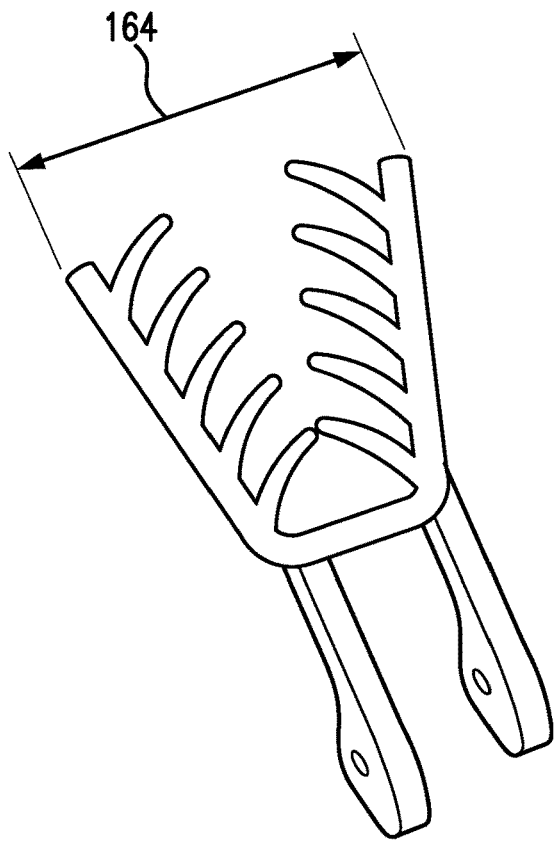
Figure 18C:
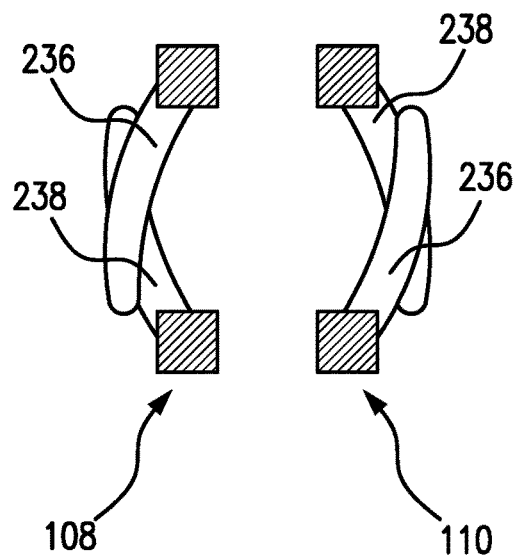
FIG. 18C is a cross-sectional end view of two of the alternative embodiments of the deformable frame of the arm of FIGS. 18A-18B, in accordance with the disclosed subject matter.

In accordance with yet another embodiment of the disclosed subject matter having first and second flank members, and as illustrated in FIGS. 18A-18C, the deformable frame 105 of the arm 108 can comprise a plurality of first struts 236 extending laterally from the first flank member 232 toward the second flank member 234 and a plurality of second struts 238 extending laterally from the second flank member 234 toward the first strut 236 member. The plurality of first struts 236 and the plurality of second struts 238 can be configured to interlock with each other in the deformed condition, as depicted in FIG. 18A, and release from each other in the undeformed condition, as depicted in 18B. As with the embodiment of FIGS. 15A-15B, the plurality of struts 236, 238 can be configured to remain generally planar with the flank members 232, 234 in the deformed condition. The plurality of struts 236, 238 can be configured to extend in the same longitudinal direction when in the deformed condition or inter-weave in and out of plane, as depicted in FIG. 18C when in the deformed configuration. FIG. 18C illustrates a cross-sectional end view of the first arm 108 and second arm 110 in the deformed condition.

Figure 19A:
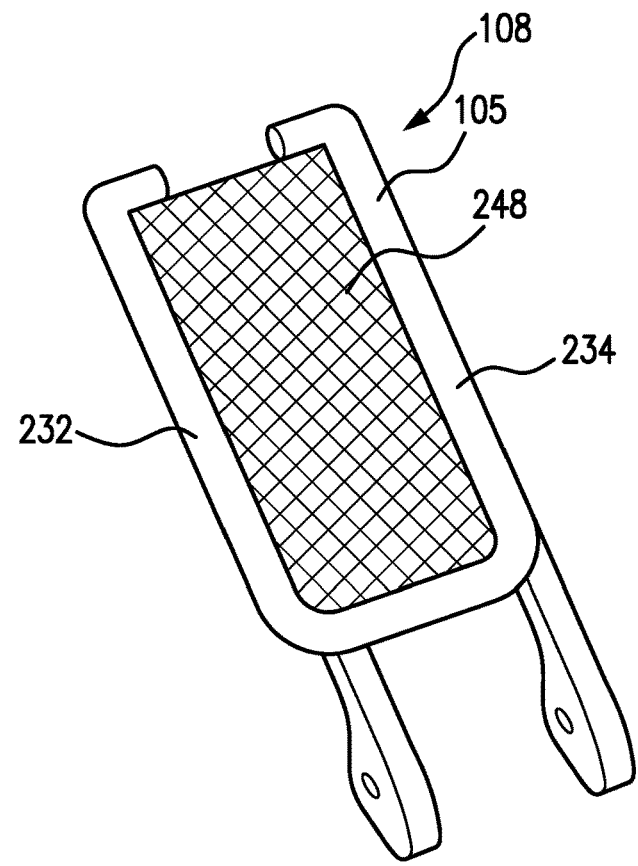
FIGS. 19A-19B are perspective views of another embodiment of a deformable frame of an arm in a deformed condition and an undeformed condition, respectively, in accordance with the disclosed subject matter.
Figure 19B:
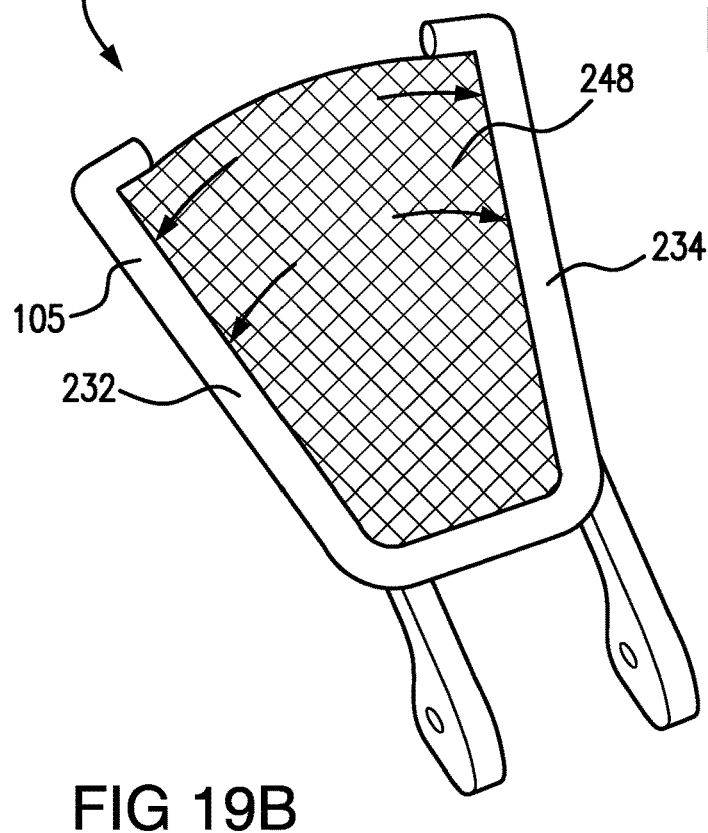

With reference now to FIGS. 19A-19B, the at least one arm 108 can additionally or alternatively comprise an expandable mesh portion 248 extending between the first and second flank members 232, 234. The expandable mesh portion can 248 can be comprised of polymeric woven materials such as polyester, poly-lactic acid, PLGA, braided metals such as stainless steel, titanium alloys, cobalt chrome, or super-elastic metal alloys such as nitinol. FIG. 19A depicts the deformable frame 105 of the arm in the deformed condition, and FIG. 19B depicts the deformable frame 105 of the arm 108 in the undeformed condition.

As previously noted, the deformable frame 105 of arm 108 of the disclosed subject matter can be biased toward the undeformed condition for automatic expansion when released from a guide catheter, outer sheath, or the like. Additionally or alternatively, the deformable frame can be formed of a shape memory material, such as Nitinol, which is heat treated to deploy by temperature. Additionally or alternatively, and as previously noted with reference to FIG. 9, the at least one arm can be manually or selectively deployed from the deformed condition to the undeformed condition by a boss or cam or the like, wherein it is recognized that the "undeformed condition" references the condition in the which the deformable frame is held in position by the boss. For example, and with reference now to FIGS. 20, additional details of the boss 258, 260 are depicted for purpose of illustration and not limitation. The boss 258, 260 is previously noted with reference to FIG. 9. Here, in FIG. 20 the boss 258, 260 is depicted in top view wherein the boss is configured to have a maximum width dimension at location 262. The fixation device can be configured such that the arms 108, 110 are proximate the boss 258, 260 with the boss disposed between the flank members 232, 234. As the arm is moved from a fully closed position toward an open position, the flank rides along the surface of the boss to expand toward an undeformed width. In this manner, the arm width can proportionally depend on the boss width such that the arms 108, 110 have a maximum undeformed arm width 164 when located proximate the maximum boss width location 262 (i.e., when the arm angle A is between about 15 to 45 degrees). Furthermore, when the arm angle is below about 10 degrees, the arm width approaches the maximum deformed arm lateral cross-dimension 165 to facilitate delivery of the device through a steerable guide catheter. FIG. 20 depicts the first arm 108 at various arm angles A and widths W1-W3. At W3, the arm angle A is relatively large such that the flank members 232, 234 are outside the maximum boss width dimension location 162. At W2, the arm angle is between 45 and 15 degrees and the flank members 232, 234 are located proximate the maximum boss width dimension location 162. At W1, the arm angle is relatively small such that the flank members 232, 234 are inside the maximum boss width dimension location 162. It is contemplated that the boss 258, 260 can also have a compressed configuration to further facilitate a reduced profile for the fixation device while in the delivery catheter.

For each embodiment disclosed herein, the fixation device can further include an assembly to move the arms between various defined positions, for example, and not limitation, and with reference to FIG. 1, the fixation device embodied herein includes two link members or legs 168, each leg 168 having a first end which is rotatably joined with one of the arms 108, 110 and a second end which is rotatably joined with a base. The base 170 can be operatively connected with a stud 176 which can be operatively attached to a distal end of a delivery shaft (not shown for clarity). In some embodiments, the stud 176 can be threaded so that the distal end of a delivery shaft can attach to the stud 176 by a screw-type action. Further, the connection point between the stud 176 and the distal end of a delivery shaft can be disposed within the coupling member 174. However, the distal end of a delivery shaft and stud 176 can be operatively connected by any mechanism which is releasable to allow the fixation device 104 to be detached. The stud can be axially extendable and retractable to move the base and therefore the legs 168 which rotate the arms 108, 110 between closed, open and inverted positions. Likewise, immobilization of the stud, such as by a locking mechanism 178, can hold the legs 168 in place and therefore lock the arms 108, 110 in a desired position. Further details are disclosed in the patents and publications incorporated by reference herein.

The embodiments illustrated herein are adapted for repair of a heart valve, such as a mitral valve, using an antegrade approach from a patient's left atrium. Prior to a procedure, imaging and various tests can be performed to anticipate and diagnose a patient's individual circumstances and assist a physician in selecting a fixation device having the desired parameters.

While the embodiments disclosed herein utilize a push-to-open, pull-to-close mechanism for opening and closing arms it should be understood that other suitable mechanisms can be used, such as a pull-to-open, push-to-close mechanism. Likewise, other actuation elements can be used for deployment of the gripping elements.

While the disclosed subject matter is described herein in terms of certain preferred embodiments for purpose of illustration and not limitation, those skilled in the art will recognize that various modifications and improvements can be made to the disclosed subject matter without departing from the scope thereof. Moreover, although individual features of one embodiment of the disclosed subject matter can be discussed herein or shown in the drawings of one embodiment and not in other embodiments, it should be readily apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A fixation device for fixation of leaflets of a heart valve comprising:
 a central assembly;
 at least one arm moveably coupled relative to the central assembly, the at least one arm comprising:
  a deformable frame having a first end and a second end and a longitudinal axis defined therebetween, the second end being moveable between a closed position and an open position, the deformable frame further comprising first and second deformable flex portions, each flex portion extending along a respective lateral side of the deformable frame and having a deformed condition and an undeformed condition, each flex portion having an outer lateral edge,
  wherein the first flex portion comprises a deformable first flank member extending longitudinally along a first lateral side of the deformable frame and the second flex portion comprises a deformable second flank member extending longitudinally along a second lateral side of the deformable frame, the first and second flank members in the deformed condition being aligned generally parallel with the longitudinal axis, wherein the deformable frame further comprises a first strut extending laterally from the first flank member to the second flank member, the first strut comprising a hinge portion having a compressed configuration with the deformable frame in the deformed condition and an extended configuration with the deformable frame in the undeformed condition, wherein the at least one arm has a maximum deformed arm lateral cross-dimension with the flex portions in the deformed condition and a maximum undeformed arm width defined between the outer lateral edge of the first flex portion and the outer lateral edge of the second flex portion in the undeformed condition, wherein the maximum undeformed arm width is greater than the maximum deformed arm lateral cross-dimension; and at least one gripping element moveable relative to the at least one arm to capture a native leaflet therebetween.

2. The fixation device of claim 1, wherein the deformable frame further comprises a trough defined along the longitudinal axis, and further wherein the first flex portion comprises a deformable first wing extension extending laterally from a first lateral side of the trough and the second flex portion comprises a deformable second wing extension extending laterally from a second lateral side of the trough.

3. The fixation device of claim 2, wherein the first and second wing extensions each has a second end edge extending laterally from the second end of the deformable frame at a second end angle defined between the second end edge and the longitudinal axis, wherein the second end angle is between 15 and 45 degrees.

4. The fixation device of claim 2, wherein the deformable frame, including the trough and the first and second wing extensions, is a single piece construction.

5. The fixation device of claim 2, wherein the first and second wing extensions each includes at least one notch defined along a respective lateral edge thereof.

6. The fixation device of claim 2, wherein the first and second wing extensions each comprises an open wing extension frame defining a wing opening therethrough in plan view.

7. The fixation device of claim 1, wherein the maximum undeformed arm width is proximate the second end of the deformable frame.

8. The fixation device of claim 7, wherein the deformable frame further comprises a trough defined along the longitudinal axis, the trough having a greater width between opposing lateral sides of the trough along a length of the arm proximate the maximum undeformed arm width.

9. The fixation device of claim 8, wherein the at least one gripping element has a first end coupled to a portion of the fixation device and a second end moveable relative to the at least one arm, wherein the gripping element has a greater width proximate the second end of the gripping element.

10. The fixation device of claim 2, wherein the first and second wing extensions are made of shape memory material.

11. The fixation device of claim 1, wherein the first and second flank members in the undeformed condition each having at least a length thereof extending outwardly away from the longitudinal axis.

12. The fixation device of claim 1, wherein the hinge portion is biased toward the extended condition.

13. The fixation device of claim 1, wherein the deformable frame further comprises an end strut extending laterally from the first flank member to the second flank member at the second end of the deformable frame, the end strut comprising a hinge portion having a compressed configuration with the deformable frame in the deformed condition and an extended configuration with the deformable frame in the undeformed condition, the first strut being spaced longitudinally from the end strut.

14. A fixation device for fixation of leaflets of a heart valve comprising:

a central assembly;

at least one arm moveably coupled relative to the central assembly, the at least one arm comprising:

a deformable frame having a first end and a second end and a longitudinal axis defined therebetween, the second end being moveable between a closed position and an open position, the deformable frame further comprising first and second deformable flex portions, each flex portion extending along a respective lateral side of the deformable frame and having a deformed condition and an undeformed condition, each flex portion having an outer lateral edge, wherein the first flex portion comprises a deformable first flank member extending longitudinally along a first lateral side of the deformable frame and the second flex portion comprises a deformable second flank member extending longitudinally along a second lateral side of the deformable frame, the first and second flank members in the deformed condition being aligned generally parallel with the longitudinal axis, wherein the deformable frame further comprises: a first strut extending laterally from the first flank member toward the second flank member and a second strut extending laterally from the second flank member toward the first strut member, wherein the at least one arm has a maximum deformed arm lateral cross-dimension with the flex portions in the deformed condition and a maximum undeformed arm width defined between the outer lateral edge of the first flex portion and the outer lateral edge of the second flex portion in the undeformed condition, wherein the maximum undeformed arm width is greater than the maximum deformed arm lateral cross-dimension; and at least one gripping element moveable relative to the at least one arm to capture a native leaflet therebetween.

15. The fixation device of claim 14, wherein the deformable frame further comprises an end strut extending laterally from the first flank member to the second flank member at the second end of the deformable frame, the end strut comprising a hinge portion having a compressed configuration with the deformable frame in the deformed condition and an extended configuration with the deformable frame in the undeformed condition.

16. The fixation device of claim 14, wherein the first and second struts are in overlapping sliding arrangement for movement relative each other between the deformed condition and the undeformed condition.

17. The fixation device of claim 14, wherein the first and second struts are laterally spaced from each other with the deformable frame in the undeformed condition, the fixation device further comprising a middle support member extending parallel with the longitudinal axis between the first and second flank members.

18. A fixation device for fixation of leaflets of a heart valve comprising:

a central assembly;
at least one arm moveably coupled relative to the central assembly, the at least one arm comprising:
a deformable frame having a first end and a second end and a longitudinal axis defined therebetween, the second end being moveable between a closed position and an open position, the deformable frame further comprising first and second deformable flex portions, each flex portion extending along a respective lateral side of the deformable frame and having a deformed condition and an undeformed condition, each flex portion having an outer lateral edge,
wherein the first flex portion comprises a deformable first flank member extending longitudinally along a first lateral side of the deformable frame and the second flex portion comprises a deformable second flank member extending longitudinally along a second lateral side of the deformable frame, the first and second flank members in the deformed condition being aligned generally parallel with the longitudinal axis,
wherein the deformable frame comprises a plurality of first struts extending laterally from the first flank member toward the second flank member and a plurality of second struts extending laterally from the second flank member toward the first strut member, the plurality of first struts and the plurality of second struts configured to interlock with each other in the deformed condition and release from each other in the undeformed condition,
wherein the at least one arm has a maximum deformed arm lateral cross-dimension with the flex portions in the deformed condition and a maximum undeformed arm width defined between the outer lateral edge of the first flex portion and the outer lateral edge of the second flex portion in the undeformed condition, wherein the maximum undeformed arm width is greater than the maximum deformed arm lateral cross-dimension; and
at least one gripping element moveable relative to the at least one arm to capture a native leaflet therebetween.

19. The fixation device of claim 14, wherein the first and second flank members each has a tapered portion proximate the second end of the deformable frame.

20. The fixation device of claim 14, the at least one arm further comprising:
an expandable mesh portion extending between the first and second flank members.

21. The fixation device of claim 18, wherein the first and second flank members comprise shape memory material.

* * * * *